(12) United States Patent
Koenig

(10) Patent No.: US 7,167,855 B1
(45) Date of Patent: Jan. 23, 2007

(54) INTERNET-BASED MATCHING SERVICE FOR EXPERT CONSULTANTS AND CUSTOMERS WITH MATCHING OF QUALIFICATIONS AND TIMES OF AVAILABILITY

(76) Inventor: Richard Koenig, 10300 Cavanaugh Ct., Rockville, MD (US) 20850

( * ) Notice: Subject to any disclaimer, the term of this patent is extended or adjusted under 35 U.S.C. 154(b) by 27 days.

(21) Appl. No.: 09/636,547

(22) Filed: Aug. 11, 2000

Related U.S. Application Data

(63) Continuation-in-part of application No. 09/418,474, filed on Oct. 15, 1999, now abandoned.

(51) Int. Cl.
*G06F 17/30* (2006.01)

(52) U.S. Cl. .............................. 707/3; 707/6; 707/104.1
(58) Field of Classification Search ...... 707/100–104.1, 707/1–10, 200–206
See application file for complete search history.

(56) References Cited

U.S. PATENT DOCUMENTS

| | | | |
|---|---|---|---|
| 5,117,353 A | 5/1992 | Stipanovich et al. | |
| 5,164,897 A | 11/1992 | Clark et al. | |
| 5,704,044 A | 12/1997 | Tarter et al. ................ | 395/204 |
| 5,784,539 A | 7/1998 | Lenz ........................... | 395/50 |
| 5,787,443 A | 7/1998 | Palmer ....................... | 707/202 |
| 5,802,511 A * | 9/1998 | Kouchi et al. ................. | 707/2 |
| 5,832,497 A | 11/1998 | Taylor | |
| 5,862,223 A | 1/1999 | Walker et al. ................ | 380/25 |
| 5,862,325 A | 1/1999 | Reed et al. ............ | 395/200.31 |
| 5,913,210 A | 6/1999 | Call | |
| 5,935,060 A | 8/1999 | Iliff ............................ | 600/300 |
| 5,948,054 A | 9/1999 | Nielsen ....................... | 709/200 |
| 5,950,200 A | 9/1999 | Sudai et al. .................... | 707/9 |
| 5,970,502 A | 10/1999 | Salkewicz et al. .......... | 707/201 |
| 6,076,091 A * | 6/2000 | Fohn et al. ................. | 707/102 |
| 6,078,891 A * | 6/2000 | Riordan et al. ............... | 705/10 |
| 2003/0097291 A1 | 5/2003 | Freedman | |

OTHER PUBLICATIONS

Information from Web site of kforce.com, as of Oct. 27, 1999.
Yahoo Finance Profile—Romac International, Inc., as of Oct. 27, 1999.
Yahoo/Market Guide–Romac International, Inc., Oct. 29, 1999.
Information from the Web site of kforce.com, Oct. 29, 1999.
Copy of International Search Report Jan. 4, 2001.

\* cited by examiner

*Primary Examiner*—Joon Hwan Hwang

(57) ABSTRACT

An Internet server matches experts offering consulting services in the biological sciences or the like with potential customers of such consulting services. The server presents each expert with a Web interface through which the expert inputs his or her qualifications and times of availability. The qualifications are organized in a two-tier hierarchy of broad subject areas and sub-areas within each area. The times of availability are organized in terms of starting time of availability and duration of availability from that starting time. The server also presents each customer with a Web interface through which the customer inputs the qualification and times of availability sought. The qualifications and times are organized in the same fashion as for the expert. The customer can input multiple service requests, each with different qualifications and times of availability. The server uses the input data to match experts with customers. At first, the experts and the customers are anonymous to one another. Once either an expert or a customer chooses to purchase the record concerning a match, the record with contact information is released, and the expert and the customer can contact each other. The server provides other functions, such as allowing a physician to contact a manufacturer or a product, using only the brand name of that product; allowing companies to conduct surveys of physicians; and providing distance learning.

7 Claims, 17 Drawing Sheets individual consultant registration

[FrontPage Save Results Component]

Please provide the following contact information (my address will be kept confidential by blothink)

First name [          ]
Last name [          ]
Middle initial [   ]
Organization [              ]
Street address [              ]
Address (cont.) [              ]
City [              ]
State/Province [              ]
Zip/Postal code [      ]
County [              ]
Work Phone [              ]
FAX [              ]
E-mail [              ]
URL [              ]

BILLING
Credit card [      ▽]
Cardholder name [              ]
Card number [              ]
Expiration date [      ]

I would like to be contacted by:

☐ e-mail (primary way of communication)
☐ phone . The best time to call is [          ] hh:nn:ss am/pm
☐ fax Time zone:
[GMT - 12 hrs Eniwetok, Kwajalein          ▽]

FIG. 4A

Personal Information

I am interested in:

☐ consulting opportunities in my area of expertise
    ☐ learning more about permanent job opportunities
    ☐ learning more about temporary job opportunities
    ☐ serving as a medical expert for industry or others I am available for consulting:

○ Immediately
    ○ In 1 week from now
    ○ In 2 weeks from now
    ○ In 2-4 weeks from now
    ○ In 4-8 weeks from now I am available for a temporary job:

○ Immediately
    ○ In 1 week from now
    ○ In 2 weeks from now
    ○ In 2-4 weeks from now
    ○ In 4-8 weeks from now I am available for a permanent job:

○ Short term (0-3 months)
    ○ Maybe later (3-6 months)
    ○ Maybe later (6-12 months)
    ○ Keep me posted about opportunities Length of availability - I will be available for consulting for:

○ 1 week
    ○ 2 weeks
    ○ 2-4 weeks
    ○ 4-8 weeks
    ○ flexible
    ○ as the project requires I have the following geographic preferences for working with clients:

FIG. 4B

| ☐ New York Metro | ☐ San Francisco (Bay Area) | ☐ Washington DC Metro | ☐ Boston Metro |
|---|---|---|---|
| ☐ New Jersey | ☐ Pennsylvania | ☐ Chicago Metro | ☐ NW |
| ☐ NE | ☐ SW | ☐ SE | ☐ Southern California |
| ☐ anywhere in the US | ☐ Europe | ☐ Asia Pacific | ☐ Americas |

Your education/certification (check all that apply):

| ☐ MD | ☐ LPN |
|---|---|
| ☐ PhD | ☐ BS |
| ☐ RPh | ☐ RAC |
| ☐ RN | ☐ MBA |

Other degree or certification:

[                    ]

Industry experience:

○ <2 years
  ○ 2-5 years
  ○ >5 years

Memberships:

☐ AMA
  ☐ AMWA
  ☐ DIA
  ☐ FDLI
  ☐ RAPS
  ☐ Other

Number of professional presentations/classes you've taught or organized:

○ none
  ○ <5
  ○ >5

Number of publications you've authored or co-authored:

FIG. 4C

○ none
○ <5
○ <10
○ <20
○ >20

[Submit Form]  [Reset Form]

Copyright 1999 Biosciences Corp.
Last revised: August 27, 1999

FIG. 4D

Individual expert questionnaire

Your expertise if focused in:

[Business Development ▽][Go]

FIG. 5

Fig. 6 ⌐600 individual expert registration

Your expertise:

Business Development         Level of Skill

| | 1 | 2 | 3 | 4 | 5 |
|---|---|---|---|---|---|
| ☐ Integrated Due Diligence assessments | O | O | O | O | O |
| ☐ Business opportunity identification | O | O | O | O | O |
| ☐ Business strategy | O | O | O | O | O |
| ☐ In-licensing | O | O | O | O | O |
| ☐ Out-licensing | O | O | O | O | O |
| ☐ Portfolio and Product analysis | O | O | O | O | O |
| ☐ Licensing negotiations | O | O | O | O | O |
| ☐ Product acquisitions | O | O | O | O | O |
| ☐ Mergers and acquisitions | O | O | O | O | O |
| ☐ Financial modeling | O | O | O | O | O |

[ Submit Form ]    [ Reset Form ]

Copyright 1999 Biosciences Corp.
Last revised: August 27, 1999

Fig. 7 ⌐700 individual expert questionnaire

Thank you very much for registering with Bio Think regarding your primary area of expertise.

If you have a secondary or tiertiary area of expertise, please select it below and answer the questions.

[ Business development ▼ ] [Go]

Otherwise, please click here to return to the main Bio Think page for more news about the allied disciplines of biotechnology, medical devices and pharmacology.

INTERNET-BASED MATCHING SERVICE FOR EXPERT CONSULTANTS AND CUSTOMERS WITH MATCHING OF QUALIFICATIONS AND TIMES OF AVAILABILITY

REFERENCE TO RELATED APPLICATION

This is a continuation-in-part of U.S. patent application Ser. No. 09/418,474, filed Oct. 15, 1999 now abandoned, whose disclosure is hereby incorporated by reference in its entirety into the present disclosure.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention is directed to a system and method for matching experts and expertise with persons requiring expert services and more particularly for a system and method for doing such matching by use of a database of experts' areas of expertise and times of availability.

The increasing complexity of product development and business building in the biosciences (biotech, pharmaceutical and medical device industry) requires more and more integration of specialized knowledge to achieve business goals. Overall R&D expenditures in the pharmaceutical, medical device and biotech industry in the US alone are more than $50 billion annually, out of which about $4–5 billion are currently being outsourced to outside vendors. The main outside service providers are clinical research organizations and specialized service providers in other aspects of product development and post-marketing activities. In addition, many individual consultants provide services to customers.

The trend for outsourcing of product development and post-marketing activities in the bio-sciences is accelerating as companies try to concentrate more and more on core competencies and outsource other activities.

Product development (new drugs, medical devices and biologics) is an expensive and time-consuming business. It is heavily regulated by government authorities in virtually all countries in the world, with the European and US authorities setting the framework for data generation, scientific review and marketing authorization standards. Because of the similarities in product development and product maintenance, the underlying strategies for data generation and assembly of supportive dossiers for product approval purposes are virtually identical in nature in all industrialized countries of the world, specifically in the US, Canada, Australia, the European countries and Japan. Other Asian countries and countries in South America follow the lead of these countries.

The time to market—from product concept through marketing approval by a government agency—is critical to the overall return on investment for firms that develop new products. Typical product development cost range from $50 million to $ 300 million for pharmaceuticals and biotech products, and less for medical devices (depending on the use of the device), and development times range from 2 years to more than 10 years.

Any shortening of the time frame required to bring products to market will result not only in a competitive advantage ("first to market"), resulting in a larger market share than competitors that enter the market later, but also in an improved return on investment. Shortened development times will then translate into higher product profitability, earlier break even on the R&D investment, and a higher profitability of the enterprise with all its positive impact on earnings per share and subsequently share price.

This is certainly not a new insight, and companies have tried to address this issue by outsourcing more and more developmental activities (pre-clinical studies, clinical development) in an effort to tighten the developmental timelines and reduce cost for internal personnel needed for an efficient in-house development.

With the ever increasing number of service providers, customers (pharmaceutical, medical device and biotech firms) now have a choice among several service providers in the same service segment. However, the marketplace for services is very inefficient and relies heavily on conventional sales and business development activities on the part of service providers. That inefficiency contributes to a bloated cost structure of these service provider. That cost, of course, is ultimately borne by the corporate customer (the firm using service providers) and thus offsets somewhat the desired savings on the part of the customer. Even with high cash payments to purchase services, customers still have the hope of an improved product development and time to approval as compared to an in-house development.

However, in reality, comparisons between the cost-structure, corporate performance and track record, as well as available resources and their training standard, are not always made by the customer, mainly because the task of selecting a service provider is very complex and time consuming for internal personnel. This involvement of key personnel may in fact slow down other activities in product development so that the net effect of using outside service providers as far as time savings is concerned, may not be that significant as hope for by the customer.

Customers usually do not have access to broad comparisons of different service providers, including their strengths and weaknesses, unless they go through a usually time consuming selection and verification process. In addition, it is uncommon for customers to have an overview over pricing information for comparable services among service providers as well as information on available capacity of service providers at a given time. It may very well be that excess capacity of a certain service provider may result in a price break for a customer, so that the service provider is able at least to sell the available capacity at a reduced rate rather than not sell it at all. Conversely, in times of full utilization of capacity in the service provider universe, capacity for certain services may be available only at a premium and may only be allocated to the party willing to pay that premium because internal time constraints require a tradeoff between more expenses today or a later product market introduction with delayed revenue stream in the future.

Solutions to some of the above problems have been sought on the Internet. In recent years, as the Internet and especially the World Wide Web have attracted the attention of commercial interests, many venues have been formed to match users with complementary goals. In Usenet newsgroups, and later on Web sites, people have offered or sought everything from antique fountain pens to love. Such matching has also extended to the matching of those offering expert skills with those requiring such skills. Two such systems are taught in U.S. Pat. No. 5,862,223 to Walker et al and U.S. Pat. No. 5,948,054 to Nielsen.

Walker et al teaches a system and method for matching experts with customers. A customer can log onto the system and successively choose a subject area (e.g., medicine), a subcategory (e.g., pediatrics), an expert level (e.g., a general practitioner), and an individual expert or experts. The experts' qualifications beyond the subject area, the subcategory, and the expert level are stored in an expert qualifications database, which can be in multimedia form (e.g., text, video, audio) and transmitted to customers; alternatively, the system can search the expert qualifications database through any of a variety of search protocols to weed out, e.g., mathematicians who have not published papers in number theory. The price and time frame can be included in the customer's question, but the time frame is limited to a "response time $\leq 2.0$ hours" format. The selected experts are notified and have the opportunity to submit bids. The expert's answer is routed through the system, which also handles payment. Nielsen teaches a matchmaking system in which customers having questions are matched with experts. However, the matching is done between a the customer's natural-language question and a natural-language statement of each expert's qualifications. Also, the times during which each expert will be available are not stored.

Another problem occurs when a person, such as a physician, wishes to obtain information a product by its trade name. The person wishing the information must determine the name of the manufacturer using the trade name, locate contact information and use that contact information to ask the question. That process is time-consuming, and if the manufacturer is a large corporation with multiple locations, the question may not reach anyone qualified to answer it.

One possible solution to that problem is taught by U.S. Pat. No. 5,913,210 to Call. Call teaches an Internet system for delivering information about products from the source of those products. A product code translator stores cross-references between UPC codes and Internet addresses for locations of information about the products. When an incoming query is received, a table lookup function is performed for a set of UPC codes comprising the code or codes contained in the query. If there is a match, the URL's found in the search are returned to the person submitting the query. If the URL for a particular company is an e-mail address, the e-mail can be forwarded to the company. Alternatively, the URL can be a Web page of product information.

However, Call has the following shortcomings. First, the SMTP server simply generates and sends an e-mail message; there is no tracking of the status of responses. Second, the person submitting the query must have a sample of the product handy in its original packaging or otherwise be able to find out the UPC. Third, while it would be useful to integrate such a system with one for allowing queries to go in the opposite direction, there is no such integration.

SUMMARY OF THE INVENTION

In light of the above, it will be readily apparent that a need exists in the art for an efficient marketplace for expert services. It is therefore a primary object of the invention to provide a marketplace for expert services that allows experts and customers of expert services to find one another readily.

It is a further object of the invention to provide such a marketplace in which data are gathered on the experts' qualifications and stored in a readily searchable manner.

It is a still further object of the invention to provide such a marketplace in which both the experts' qualifications and their times of availability are stored, thereby providing an overview of available expertise and its availability over time.

To achieve the above and other objects, the present invention is directed to a technique for matching providers of expert services to customers needing such services. Both the providers and the customers subscribe to the service. The providers provide information on their qualifications to a database through a hierarchical menu system and also indicate the times during which they will be available. An employee of the company providing the matching calls the providers to verify the accuracy of the input data, which are then made available for searching. Thus, the database provides a profile of what resources are available and when they are available. The database can be used to provide an anonymous match between providers and customers. Once providers and customers are matched, a customer can decide to purchase the records relating to one or more providers. Upon payment, the record of the party able to provide services is released to the purchaser of that record. Before purchase, the experts and the customers are anonymous to one another. The technique can be implemented on the World Wide Web, on any other suitable Internet protocol, or on a communication system separate from the Internet.

The utility of the present invention will be illustrated in the area of biosciences as an illustrative example. However, the present invention has utility in all scientific and other areas where knowledge is to be provided to customers who need knowledge services in research and development and in the commercialization of products and services.

The invention further provides the ability for health care professional to execute an informational query to the corporate subscribers and vice versa. In this example, the parties in this information process are seen as information providers and information customers (expert consultants and customer). The role of these two parties can change based on the situation: Information providers can become information customers and vice versa. This facility will enable a health care professional to format a targeted request for information regarding a manufacturer's product, request samples, or initiate a personal contact with a manufacturer's representative.

Additional queries may be formatted at the user's discretion. The query engine will accept free form query components and direct them to the appropriate corporate entity. A list of corporate subscribers is available to the health care subscriber and they may select one or multiple corporate entities for their query. Most query entries will be directed at a specific manufacturer or bioscientific organization, but there may be instances where a health care subscriber might want to initiate a more generic query and receive responses from multiple companies.

The invention thereby provides a system that identifies the manufacturer of a specific product by using the product trade name alone. Then, the end-user (in this case, the health care provider), will relay the information request to the manufacturer. Specifically, in the case of a physician requesting or reporting information to a health care product manufacturer, the physician would use a website to enter the product name and a message. A database connected to the website would then identify the manufacturer by using the entered trade name of the product. The database would also identify the appropriate contact information (specifically the e-mail address) of the group within the health care product manufacturer that provides information or collects information on the use of its products (usually the Medical Information Department or Product Safety Department). Using the tradename of a product is a unique identifier of the manufacturer, so information could be relayed reliably.

The physician would then transmit the appropriate information or information request to the company. The communication would then be relayed to the company, preferably to a central point of contact (product safety or medical information departments).

At this point, the company specialists, dealing with the specialty issue (drug safety, medical information or another specialist knowledge area), will contact the physician by either e-mail or any other means of communication.

This aspect of the invention enables requestors of specialist knowledge and providers of feedback information on products to use the product identifier to contact the manufacturer directly, without knowing or having to know the specific contact information for the manufacturer. This will enable users of products to quickly and in an uncomplicated fashion relay feedback on products and services to the manufacturers and to request additional information, and to establish other means of communication with then manufacturer.

The query system collects information from multiple entities (in this case physicians in hospitals and private practice) via a simplified process that only requires the entry of the tradename of a product to be connected to the specific manufacturer of a product. This will then enable the manufacturer—who also possess the expert knowledge on the use of the manufacturer's products—to use the appropriate internal expert knowledge resources and to provide that information to the party providing or requesting the information.

The information resources of a manufacturer can be accessed by populating a database with information already known in the public domain. In the case of product information in the health care arena, on would use information published on products and manufacturers in the Physician's Desk Reference (PDR). Other countries have similar compendia that detail product properties and manufacturer information.

The database that would match physician requests or physician reporting would simply be populated with the information that is available in the public domain (in the PDR or equivalent publications in either hard copy or electronic format).

Information can be transmitted to or received from entities providing or needing information by using a web-based data entry form that uses the product or service tradename to identify the provider or entity that needs knowledge information. The database making the connection would be populated by publicly available information, providing the link to manufacturers or knowledge providers.

Another feature of the invention is the results response engines within the web site. This engine will enable the physicians, researchers, nursing professionals, and other key participants to respond to a corporate survey. The health care professional or researcher will access the system, select the specific corporation and the results response function. The results response engine will select the appropriate company, and if more than one results response entry exists, will provide a drop down list of the proposed response entry document. The respondent will then select from this list for the results entries that they are providing.

At the initial start of the response process, the results response engine will create a temporary storage repository for the respondent entries. This repository will be linked to the respondent's userid and the specific corporate entity identifier. The respondent's entries are then stored in this repository until the processing is completed, and the corporate entity has retrieved the completed response.

Respondent entries may be halted or paused at any point in the questionnaire or survey process. The engine will place a book mark at the point of last entry and will resume the process at the next entry point when the respondent returns to the questionnaire activity.

Still other uses for the invention include distance learning.

BRIEF DESCRIPTION OF THE DRAWINGS

A preferred embodiment of the present invention will be set forth in detail with reference to the drawings, in which:

FIGS. 4A–4D show a Web page for data in during registration;

FIGS. 5–7 show Web pages for inputting data about a user's qualifications;

DETAILED DESCRIPTION OF THE PREFERRED EMBODIMENT

Figure 1:
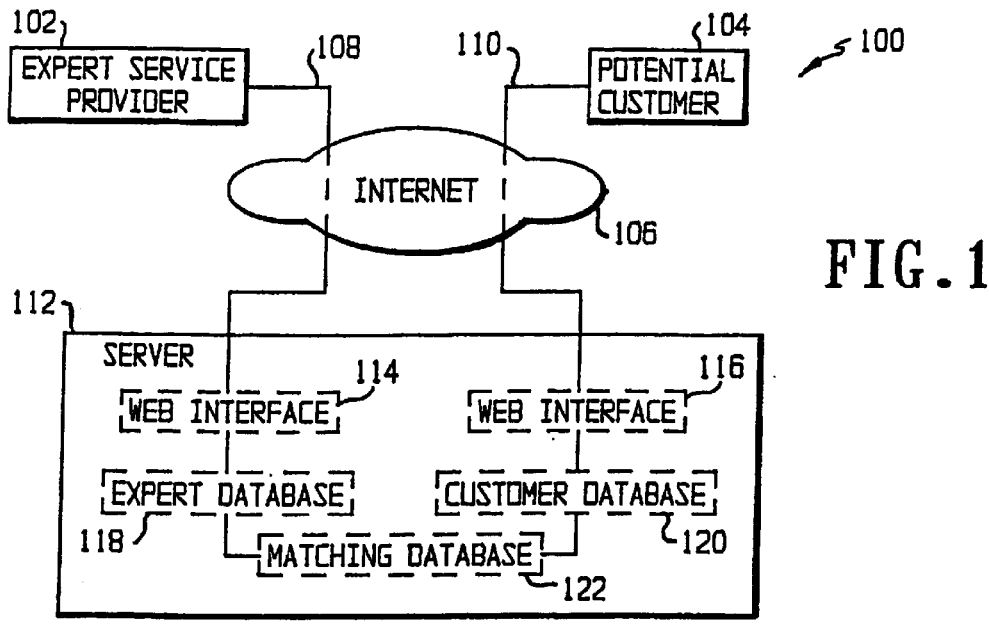
FIG. 1 shows an overview of a system implementing the preferred embodiment.

A preferred embodiment will now be set forth in detail with reference to the figures, in which like reference numerals refer to like elements throughout.

FIG. 1 shows an overview of the preferred embodiment, which is implemented on the Internet. A provider of expert services 102 and a potential customer of expert services 104 are connected to the Internet 106 through Internet connections 108, 110, which can be any type of Internet connection, from dial-up to high-speed optical connections. Of course, both the expert service provider 102 and the potential customer 104 can use any type of microcomputer or other device capable of accessing the Internet.

The expert 102 and the potential customer 104 are connected over the Internet 106 to a server 112 that determines whether they match. The expert 102 and the customer 104 are provided with a URL through which they log in and access an expert Web interface 114 and a customer Web interface 116 respectively. The Web interface 114 asks the expert 102 a series of questions to gather data on the expert 102 for an expert database 118, while the Web interface 116 asks the customer 104 a different series of questions to gather data on the customer 104 for a customer database 120. The matching between the expert database 118 and the customer database 120 results in a matching database 122 listing which experts are a match for which customers.

The Web interfaces, which will be described in greater detail below, can be implemented in any suitable manner, e.g., by CGI, while the databases, which will also be described in greater detail below, can be implemented in any suitable manner, e.g., by SQL. The server 112 can be any suitable Internet server capable of running such processes. The specific software and hardware requirements will be familiar to those skilled in the art.

Figure 2:
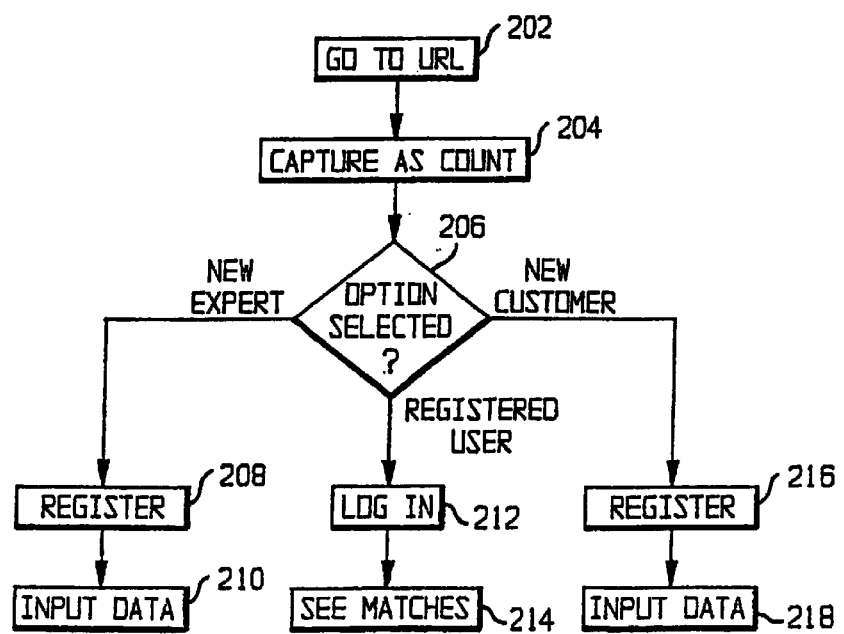
FIG. 2 shows a flow chart of operations for accessing the service.

FIG. 2 shows a broad overview of the manner in which the expert 102 and the customer 104 interact with the system 100. In step 202, a user (either the expert 102 or the customer 104) goes to the server 112 in any suitable manner, e.g., by entering the URL manually into a Web browser, by following a link from another Web page maintained by the company operating the server 112, or by following a link from an off-site Web page. In step 204, server captures the access as a count with a date/time stamp and optionally with the user's IP address and other identifying information.

In step 206, the user selects one of three options: registration as a new expert, logging in as a registered user, and registration as a new customer. The new expert registers in step 208 and inputs the data for the expert database 118 in step 210. The registered user logs in with the already established user name and password in step 212 and sees matches from the matching database 122 in step 214. The new customer registers in step 216 and inputs the data for the customer database 120 in step 218.

Figure 3:
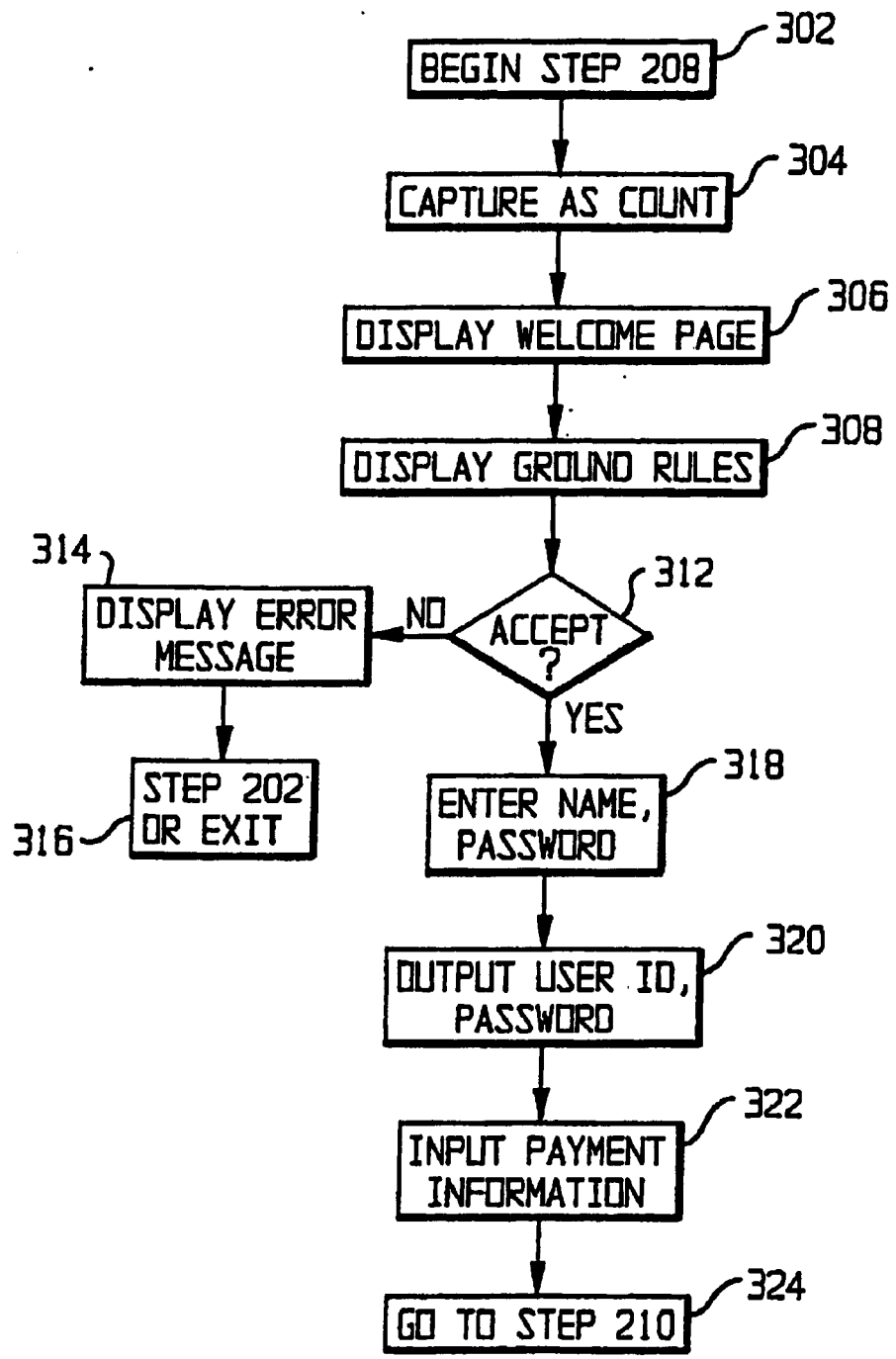
FIG. 3 shows a flow chart of operations for registering with the service.

FIG. 3 shows the steps involved in the registration 208. The user can register as an individual or as an organization; the substance of the registration procedure is the same for both options.

The registration begins in step 302. In step 304, a count is captured, as in: step 204. In step 306, a welcome page is displayed. The welcome page can display a "continue" link to let the user go to the next page or can be configured with a meta tag to go to the next page automatically after a certain time. Either way, in step 308, the next page is displayed, which sets forth the ground rules for use of the service. The user is given the opportunity to accept or decline the ground rules. If it is determined in step 312 that the user has declined the ground rules, a page is displayed in step 314, having an error message explaining the need to accept the ground rules. In step 316, the user is given the option of returning to step 202 or exiting altogether.

If it is determined in step 312 that the user has accepted the ground rules, the user enters a name and a password in step 318. The system generates a new user I.D. and password and displays them to the user in step 320. The user inputs payment information in step 322, indicating the method of payment (typically a credit card) and the length of the subscription that the user is ordering (typically one month). In step 324, the user proceeds to step 210 of entering the data. Of course, a variety of registration techniques are known in the art and can be used.

Step 210 is carried out through the use of a succession of Web pages that prompt for and receive information. The information can be received through well known techniques such as CGI.

The collection of information starts with the collection of information on contact, billing, availability and education. The billing information can be used for extra-cost services not covered by the subscription or for any other billing purposes.

Such information is collected through the page 400 shown in FIGS. 4A–4D. Of particular interest are the areas 402, 404, 406, and 408 in FIG. 4B, which collect information on times of availability. In the area 402, the user indicates whether he or she will be available for consulting immediately, in one week, in two weeks, in 2–4 weeks, or in 4–8 weeks, while the area 404 lets the user make the same choices for availability for a temporary job. In the area 406, the user can indicate availability for a permanent job. In the area 408, the user can indicate the length of time of availability for consulting, namely, one week, two weeks, 2–4 weeks, 4–8 weeks, "flexible," and "as the project requires." Thus, the areas 402 and 408 allow the user to indicate the start and stop dates for availability for consulting.

Information on the user's expertise is then collected. The various areas of expertise are organized in a two-tier hierarchy. That is, the user selects a broadly defined area of expertise and then selects one or more sub-areas within that area.

For selection of the broad area, the user is presented with the page 500 shown in FIG. 5. The page 500 includes a drop-down box 502 listing the various areas of expertise from which the user selects the primary area of expertise. As shown in FIG. 5, "Business development" is selected. Once the user selects an area, the user is presented with a page such as the page 600 shown in FIG. 6, in which the user selects one or more sub-areas within business development by checking check boxes 602. For each sub-area check off, the user can indicate his or her level of skill in a "Level of Skill" area 604, from 1 (highest) to 5 (lowest). The "Level of Skill" area 604 is shown as using radio buttons 606, although any other suitable interface, such as drop-down boxes, can be used instead. After selecting the sub-areas within the primary area, the user has the option of selecting secondary and tertiary areas of expertise through the page 700 shown in FIG. 7. Of course, for the secondary and tertiary areas, the user also selects sub-areas and a level of expertise in each sub-area.

The result is the following data structure for the expert database 118. The fields include all of the options listed in the page 400, along with each area and all of its sub-areas. Each of the fields corresponding to a time of availability can have as its value a logical "true" or "false," while each of the fields corresponding to a text box (e.g., address) can have as its value a text string of up to a specified length, and each field corresponding to a sub-area of expertise can include the skill level. The specifics of the database will be explained below with reference to FIG. 19. A staffer of the company operating the server 112 can telephone the user to verify the input information.

Figure 8:
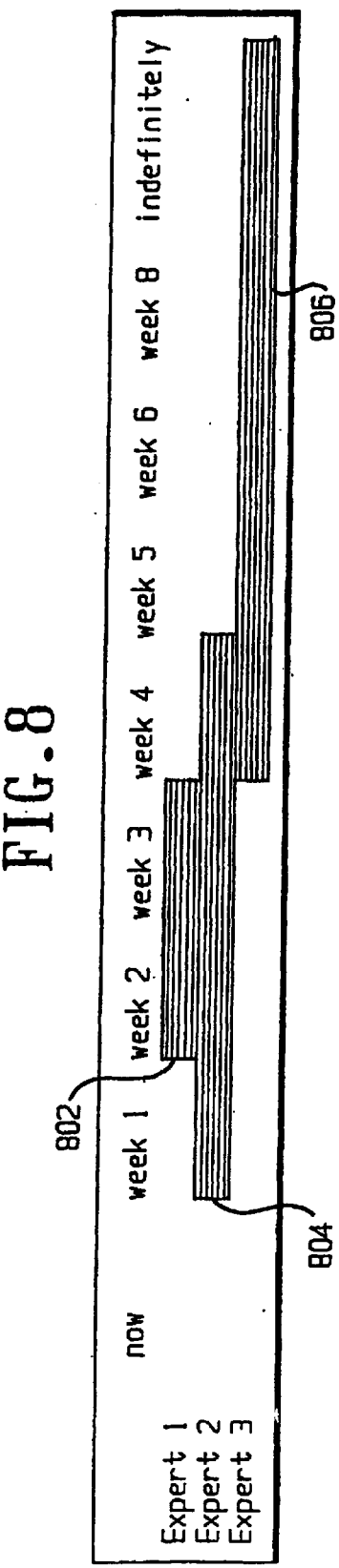
FIG. 8 shows periods of availability for three experts.

The longitudinal picture of availability can be visualized as shown in FIG. 8. Expert 1 has clicked "I am available for consulting in two weeks from now" in the area 402 and "I will be available for consulting for two weeks" in the area 408; thus, Expert 1's availability can be graphed as the bar 802. Expert 2 has clicked "I am available for consulting in one week from now" in the area 402 and "I will be available for consulting for 2–4 weeks" in the area 408; thus, Expert 2's availability can be graphed as the bar 804. Expert 3 has clicked "I am available for consulting in 4–8 weeks from now" in the area 402 and "I will be available for consulting for as long as the project requires" in the area 408; thus, Expert 3's availability can be graphed as the bar 806. Of course, a chart like that of FIG. 8 does not have to be stored, as it can quickly be rederived from the logical "true" and "false" values stored in the database 118. The customer's required times for availability can be visualized in the same manner and can be derived from the logical "true" and "false" values stored in the database 120.

The registration and data input steps 216 and 218, the Web pages associated therewith, and the resulting data structure for the customer database 120 are basically the same as those just described, except that the customer, instead of inputting its own availability times and qualifications, inputs the availability times and qualifications required for the project at hand. Records in the expert database 118 are matched with those in the customer database 120 to provide the matching database 122. The server 112 can be configured to search only for exact matches or for exact and approximate matches. If approximate or "soft" matches are allowed, they can be ranked by percentage, as known in the art of Internet search engines. If a customer 104 needs experts 102 in different areas or sub-areas of expertise, e.g., for different projects, the customer 104 can go through the data collection process multiple times, thereby submitting multiple service requests.

Another feature that can be provided at this point is the ability of a customer to rank the priority, the desired skill level or both of each category and subcategory. Referring to the sample subcategories of FIG. 6, if it is vitally important that the expert be familiar with business strategy, but only marginally important that the expert know anything about product acquisitions, the priorities can be set accordingly. Similarly, a customer can decide that a maximum skill level is needed in business opportunity identification, but any level of skill will do in mergers and acquisitions. It is contemplated that the customer will be prompted to supply both a priority and a desired skill level in each category and subcategory. The use of such priorities and skill levels in computing a match will be set forth below.

The matching process will be explained with reference to FIGS. 9 and 10. In these figures, logical "true" and "false" values are shown as ones and zeroes, respectively.

Figure 9:
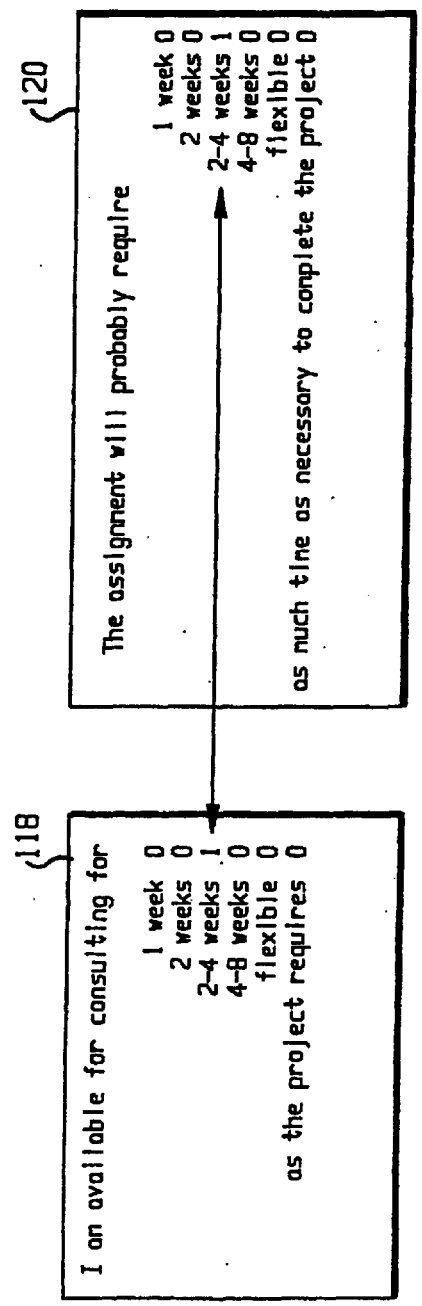
FIGS. 9 and 10 show matching between an expert database and a customer database.

FIG. 9 shows matching for the start times for availability. The expert has indicated availability for 2–4 weeks; therefore, the database 118 stores a one in that field and zeroes in the other "I am available for consulting for . . ." fields. The customer wants an expert for an assignment that will probably require 2–4 weeks; therefore, the database 120 stores a one in that field and zeroes in the other "the assignment will probably require . . ." fields. The ones and zeroes are compared, and in this case, a match is found. If the expert had indicated availability for one week, and the customer had sought an expert for 4–8 weeks, the two would not be matched.

Figure 10:
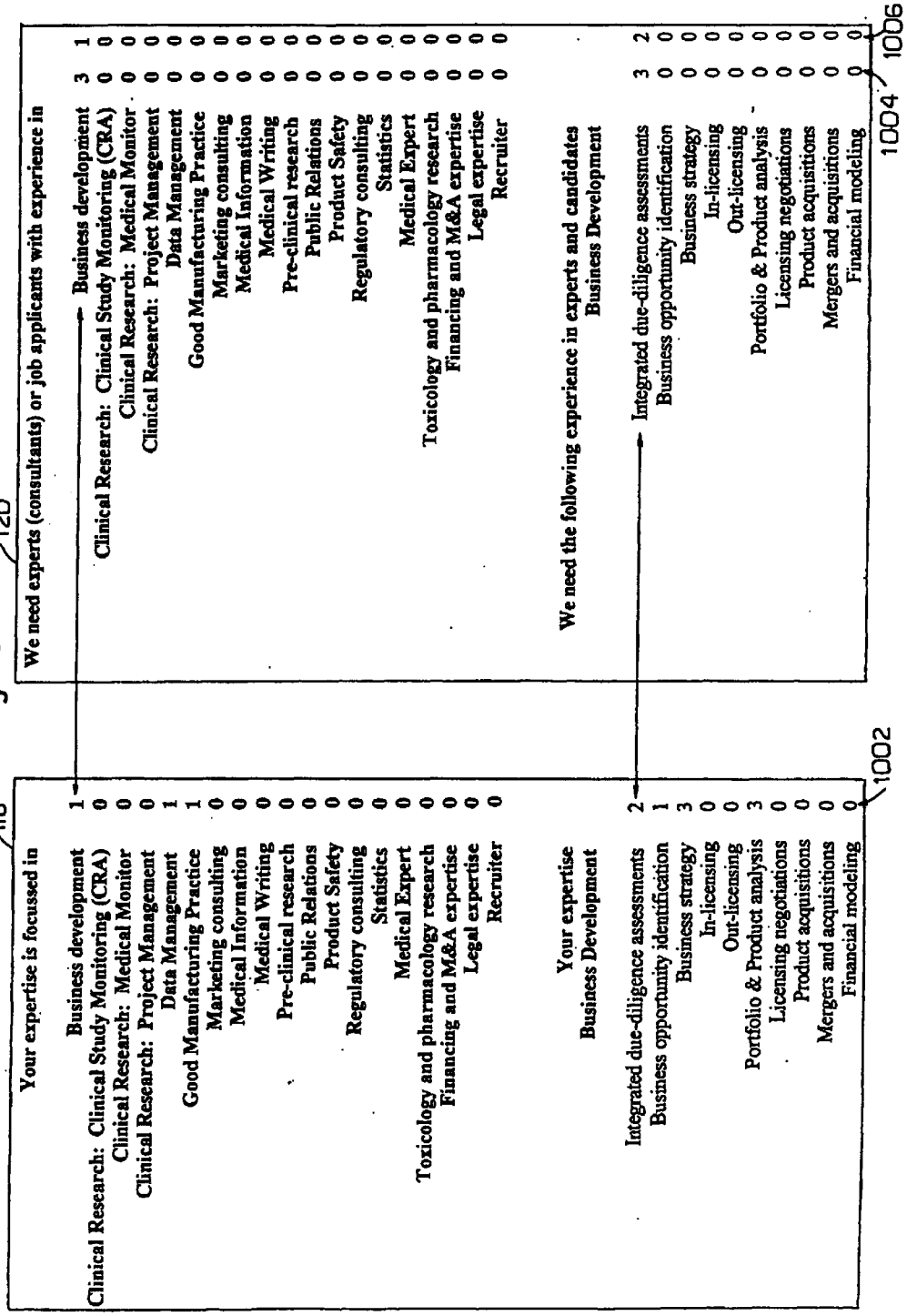

FIG. 10 shows matching for expertise. Skill and priority levels are identified as 1 (highest) to 5 (lowest), with 0 indicating no entry. The expert's skill levels are shown in column 1002, while the desired skill levels and the priority assigned by the customer to each skill level are shown in columns 1004 and 1006. The database 118 stores the information that the expert has indicated the highest level of expertise in the areas of business development, data management, and good manufacturing practice, and within the area of business development, levels 1–3 of skill in the sub-areas of integrated due-diligence assessments, business opportunity identification, business strategy, and portfolio and product analysis. The database 120 stores the information that the customer wants an expert in business development and more specifically an expert having at least the third skill level in integrated due-diligence assessments. In this case, there is a match. If the customer had wanted an expert in financial modeling, the two would not be matched.

The matching of the databases 118 and 120 to produce the database 122 can take place periodically or at least independently of times at which either the experts 102 or the customers 104 log on. One advantage of doing so is that both experts 102 and customers 104 can be notified of matches as soon as they log on, rather than having to log on and then run a matching process. Another advantage is the ability to take advantage of slow times when few users are logged on.

Figure 11:
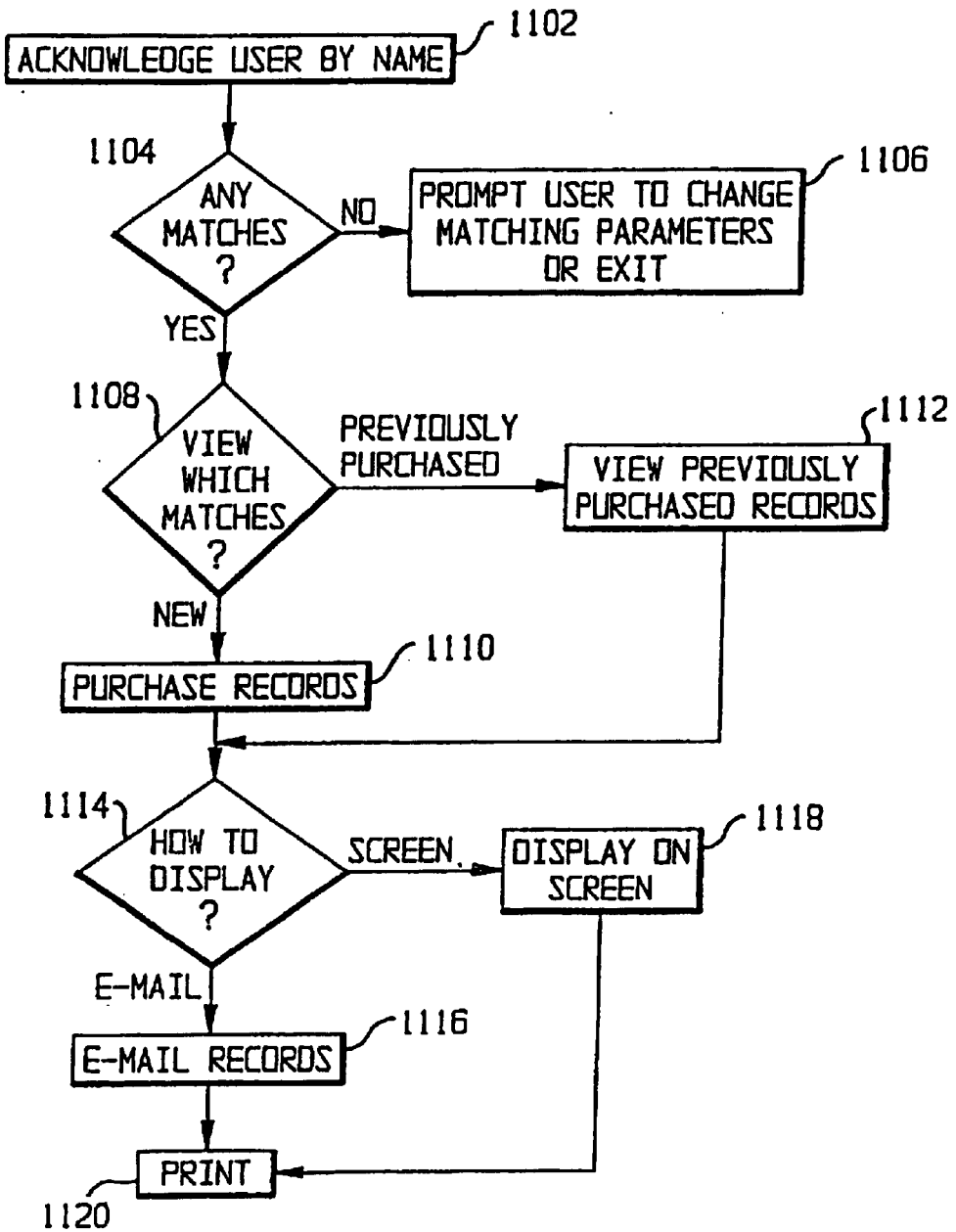
FIG. 11 shows a flow chart of operations for retrieving matches.

Step 214 of seeing the matches will now be explained with reference to FIG. 11. Once the user has logged into the server in step 212, the user is acknowledged by name in step 1102. In step 1104, it is determined whether there are any matches. If not, the user is prompted in step 1106 to change the matching parameters (e.g., by resubmitting data) or to exit and return later, when there may be matches. Any resubmitted data are stored in the customer database 120. If the user has multiple service requests, the user can be prompted in step 1106 to change the matching parameters in other service requests.

Once the user has matches, the user can purchase one or more of the records, using the payment information stored in the database 118 or 120 or other payment information. Until now, the experts and the customers have been anonymous to each other. Once a record is purchased, the contact information in that record is made available. The expert can then contact the customer, or vice versa. Other information besides contact information can be held in confidence until purchase.

In step 1108, the user is prompted to view either new matches or previously purchased matches, which can be selected by date ranges. If the user chooses to view new matches, the user is given an opportunity in step 1110 to select the matches to view and to purchase them. Once the user selects matches to purchase, the system processes the purchase on a secure server in a manner known in the online retailing art. The matches, once purchased, become available for viewing. If the user chooses to view previously purchased matches, the system allows the user to do so in step 1112. Each previously purchased match can be shown with the date of purchase and the payment information.

Whether the user wishes to view new or previously purchased matches, the user is given a choice in step 1114 to receive the records by e-mail in step 1116 or to view the records on screen in step 1118. The user can then handle the records in a suitable manner, e.g., by printing them in step 1120, using the print command of the e-mail client or Web browser.

Additional features of the preferred embodiment will now be described.

Figure 12:
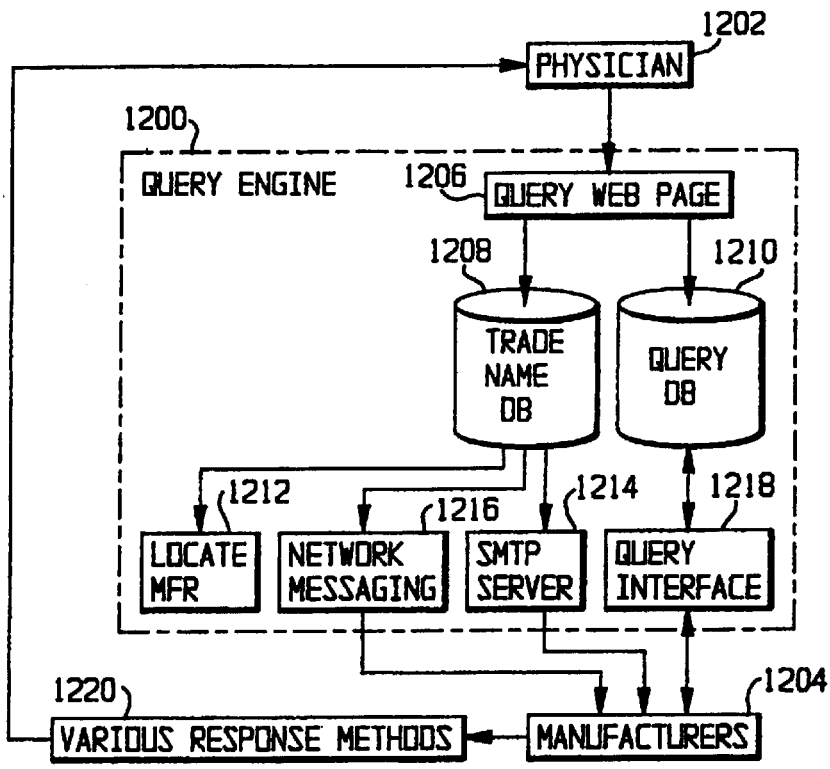
FIG. 12 shows a schematic diagram of a query engine for directing a query about a product to the manufacturer of that product.
Figure 14:
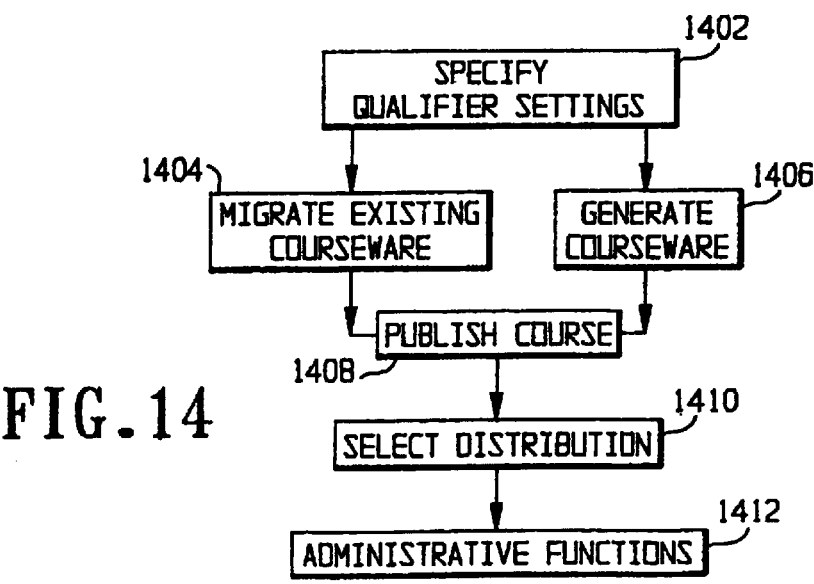
FIG. 14 shows a flow chart of operations for setting up a distance learning course.

FIG. 12 shows a flow chart of the operation of a query engine. When a physician has a question about a specific product, the physician goes to a query page on a Web site. The query page has a text box for receiving a trade name of the product and a text box for receiving a free-form query about the product. The manufacturer's contact information is determined from the trade name, and the query is forwarded. The query engine will process all inquiries from the health care professional subscribers. These inquiry records will be stored in a special repository for retrieval by the appropriate corporate client.

FIG. 12 shows the ways in which a query engine 1200 provides communication between a physician 1202 and a manufacturer 1204 of a product. It is assumed that both the physician 1202 and the manufacturer 1204 subscribe to the service offering the query engine 1200. A situation in which a manufacturer does not subscribe will be described below.

The query engine 1200 provides a query Web page 1206 having a one-line text box for entry of a trade name of a product and a free-form text box for entry of the query. When the physician 1202 completes both text boxes and clicks on a "Send" button, the query engine 1200 supplies the contents of the one-line text box to a trade name database to locate the appropriate contact information for the manufacturer 1204 and, where applicable, for a specific department in the manufacturer which handles queries for that product. The query engine 1200 also supplies the contents of the free-form text box to a query database 1210, which stores the contents of the free-form text box along with identifying information for later retrieval by a customer representative at the manufacturer 1204.

If the trade name is not located in the database 1208, an error message is generated and sent to a "locate manufacturer" process 1212. That process can either automatically attempt to locate the manufacturer or signal a human operator to do so. Either way, that manufacturer can be informed that a query has been submitted and can be invited to subscribe to the service.

When a query has been generated in the manner just described, the query engine initiates a notification process to the manufacturer 1204 by way of the contact information retrieved from the trade name database 1208. This notification will be generated as an e-mail through an SMTP server 1214 and as a network notification through a network real-time messaging server 1216 if the manufacturer is currently active on the system.

When notified of a pending inquiry by the SMTP server 1214 or the network messaging server 1216, the manufacturer logs on to the web site and select a Query icon. That icon permits the manufacturer to communicate with a query interface 1218, which retrieves all pending queries for the manufacturer 1204 and communicates them to the manufacturer 1204.

The manufacturer 1204 then selects a query to review from this list, and the query engine 1200 executes a retrieval of the related records. The query is presented to the manufacturer using a special form, and the query interface 1218 controls the query database 1210 to mark the query records as "Under Review." This will let other persons working at the manufacturer 1204 know that the specific query is currently being reviewed.

When the manufacturer 1204 has completed the review, the manufacturer 1204 may respond to the physician 1202 by any of a multiplicity of methods, collectively designated 1220. The review form will contain several options for the response. These include Direct Response, E-Mail, Document Generation, and Personal Contact. A short description of these options is show in the following paragraphs.

Direct Response: the reviewer will select the Direct Response option on the active form. This will cause the query engine to open a response window and enable the entry of the response by the reviewer. The reviewer can then enter the information requested by the health care subscriber. The entry will be free form and will allow the reviewer to enter approximately two standard pages of text.

E-mail Response: if the reviewer chooses this option, the engine will present an e-mail entry form. The query engine's e-mail form will be structured with the recipient's e-mail address already inserted in the TO: section. The reviewer may then enter their response information and press the send button to transmit the message. The communication for this facility will be totally controlled by the query engine processes. The reviewer may use this query engine mail form or may opt to log off the web site and utilize the facilities of the corporation's e-mail system. If the reviewer opts to use the Corporate e-mail facilities, he or she should use the copy function to move the requestor's e-mail address from the web site to their corporate e-mail form.

Document Generation: in the instance where the requestor requires that the corporate reviewer provide a document of some sort, the reviewer has several options.

The document may be transferred using FTP file transfer to the web site and forwarded on to the requestor.

The reviewer may inform the requester that a copy of the documentation is being sent in hard copy format via mail or delivery services.

Personal Contact: with this facility, the reviewer has the option of establishing a meeting with the requestor. This meeting can be one of several forms, as follows:

One on one personal meetings with the corporate representative setting a physical appointment to discuss the requestor's inquiry.

Telephone meeting with the corporate representative establishing a time for a telephone call to discuss the inquiry.

Video Conference with the requestor and other interested parties. This form is usually reserved for managed care or clinic staff discussions where more than one individual from the requestor's side will be involved.

There is also the option of establishing a NetMeeting or using the facilities of a Reserved Chat Room to respond to the requestor's inquiry.

The preferred embodiment also offers a corporate subscriber the option of generating surveys and questionnaires to participants in protocol testing and other research/study activity. These survey/questionnaire functions are similar in scope to the interview questionnaires described above for use by expert service providers.

Each corporate subscriber will be provided with a certain number of generation activities based on their subscription structure or profile. As questionnaire or survey forms are generated, the survey engine will update the profile entry for such generations. If the subscriber has authorization to go forward, the facility will be activated and the interview forms are created.

These survey/questionnaire forms are generated in one of two ways, depending on the desires of the corporate subscriber. The questionnaire/survey forms can be created internally by the corporate subscriber, or the subscriber can have the service's staff create and manage the interview process.

Figure 13:
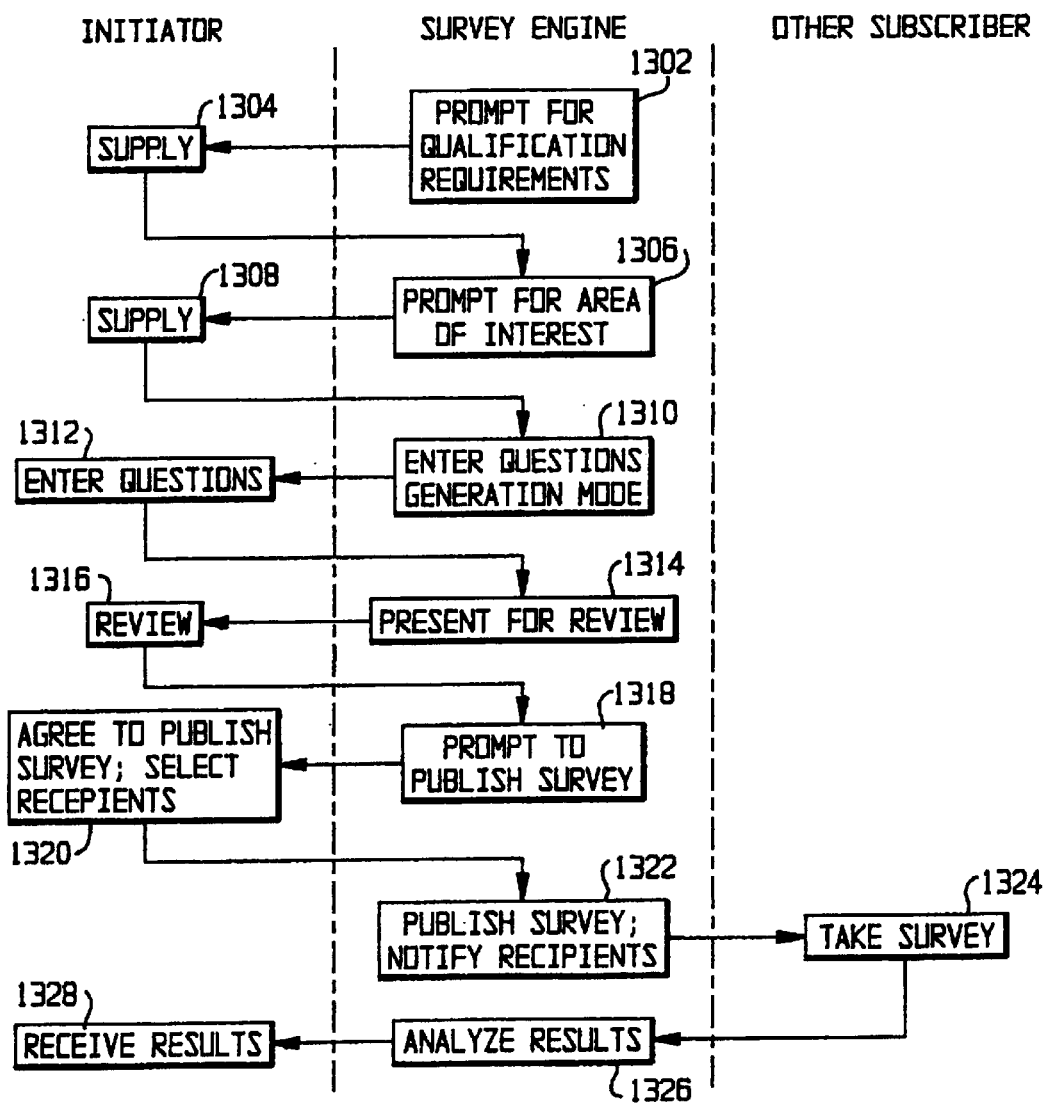
FIG. 13 shows a flow chart of operations for designing and taking a survey.

The survey engine will perform multiple tasks for the clients with regard to the processing of survey or questionnaire interviews. The process will include several features identified in the following paragraphs and shown in FIG. 13.

The engine will solicit qualification requirements from the initiator in step 1302, which the initiator will supply in step 1304. These will include items such as the specific medical discipline, area of interest, and willingness to participate in the study or testing. This set of qualifiers will be used to identify potential participants within the subscriber profiles for the health care subscribers.

The initiator may also select the option of specifying participants by name or other designator such as clinic or hospital affiliation. The initiator may also utilize a participant listing of their internal contact files.

The engine will provide an input screen that enables the initiator to define the specific area of interest for the interview process in step 1306, which the initiator will supply in step 1308. Whether this is a drug evaluation, medical procedure, medical device or other bioscientific protocol process, the initiator will be able to rapidly select the appropriate definition parameters.

The most critical aspect of the process will be the actual generation of the questions and response entries. The survey engine will enter the question generation mode in step 1310 and will display a question generation form to the initiator. The initiator will enter the actual question or statement in the space provided in the form in step 1312. The engine will then require the selection of a format type such as multiple choice, yes/no, true/false, or essay entry. If the initiator selects the multiple choice option, the engine will then accept the desired response entries and will number the entries. The initiator may enter as many responses as desired or appropriate. If the entry type selected is either yes/no or true/false, the engine will automatically insert these responses. If the entry type is an essay entry, the engine will create a free form text box entry.

When the response selection is completed, the engine will present the completed interview entries for review in step 1314. The initiator has the option of setting an entry review for each question or may set the review function to a manual process. If the initiator has set the function to a manual process, the engine will continue to accept entries without providing a review presentation until the reviewer selects the review icon. Once an entry has been reviewed and accepted, the engine will set an indicator to that effect and the specific entry will not be displayed again until the initiator requests a full review.

At the completion of an entry, the engine will ask the initiator if another entry is desired. The reviewer may select yes or no to this question. If the initiator selects yes, the engine will ask if the interview process is complete. If the initiator responds yes, the engine will close the process and prepare the final review of the entire process. If the initiator responds no to the question, the engine will mark the entries as incomplete and will set a place marker at the point of the last entry.

The initiator has the option of exiting the entire generation process and returning at any point in time. The query engine will place a book mark at the last entry processed and exit the activity. When the initiator returns to the creation process, the activity will resume at the last point of completion.

Once the initiator has completed the interview questionnaire or survey and has reviewed the survey in step 1316, the engine will provide an icon to publish the forms in step 1318. When the initiator clicks on this icon in step 1320, the questionnaire will be made available on the web site seen by physicians. The initiator has the option in step 1320 to transmit notifications to a selected list of subscribers who have indicated a desire to participate in the study. This list will be used to generate e-mail notifications in step 1322 to the health care subscribers and to other health care professionals who are not currently subscribers to the web site. The e-mail will contain an embedded URL that will connect the participant to the web site and the newly created questionnaire. The recipients of the e-mail will take the survey in step 1324. The survey engine will analyze the results in step 1326 for review by the initiator in step 1328.

The corporate subscriber may generate a survey or questionnaire using its own internal staff or the staff of the service. This facility will be provided through a special instance of the survey engine. The corporate subscriber will initiate the function by clicking on the questionnaire generation icon which will activate the questionnaire engine.

The generation engine will validate the permissions to create a questionnaire against the client profile. If the subscriber account has a positive count entry for questionnaire creation, the engine will update the entry with the current request and the positive count will be decremented. If the account entry becomes zero with the activity, the user is notified that this will be the last entry allowed under the current account status.

Each corporate subscriber will be provided with a certain number of generation activities based on their subscription structure or profile. As questionnaire or survey forms are generated, the survey engine will update the profile entry for such generations. If the subscriber has authorization to go forward, the facility will be activated and the interview forms are created.

The interview process can be activated using a distribution list of selected participants, or the engine will select participants from the client database tables based on the qualification parameters established by the client.

In the instance where the corporate subscriber determines that an outside source would be more advantageous for the generation activity, the service will assign a representative to the corporate subscriber to gather the necessary information, for the questionnaire or interview forms.

The representative will meet with the client either physically or through telephone interviews to gather the necessary information and begin the process of creating the interview forms. This process will be an additional fee for service entry and will be processed as one of the special services classifications. Cost for this service will depend on the complexity of the interview process and the number of points within the questionnaire or survey.

The representative will utilize the Questionnaire Engine to formulate the entries and generate the interview questionnaire. Once the initial questionnaire set has been completed, the representative will set up a presentation meeting with the client to review the entries and receive comments, modifications, and other input.

The final form of the interview questionnaire will be generated by the representative and registered for the corporate subscriber client. The distribution list for participants will be activated and the representative will notify the corporate subscriber client that the process is in place.

During the course of a corporate client's subscription period, there will be instances where special services will be desirable. Special services may be requested either through the web site using a service request engine or through traditional means using one on one personal contact. These services might include professional consulting services, marketing consultant services, technical web-based services, and others. If the request is generated through the web site, the following actions will take place.

The client will initiate a request for services transaction using the icon selector. This will activate the services request engine.

The services request engine will collect the client information necessary from the client profile table and establish a temporary repository in the database. This temporary repository will remain in place until the services request has been completely processed. The services request engine will then present the client with a set of forms for describing the services request.

The client will indicate the type of services required and provide a description of the scope and tasks involved based on the generated form entries from the services request engine. Any special requirements such as timeline dependencies are to be spelled out in the request.

The services request engine will process the request and notify the service that a request is waiting action. A representative will review the request with the corporate management and a determination will be made as to the appropriate response. The representative will then prepare a proposal for services using the proposal functions within the services request engine.

The proposal for services will be reviewed by the client and any changes noted using the services request engine modification facilities.

The Health Care Professionals web site will also contain a facility for continuing education activities. This facility will be supported by the Corporate clients, by professional certification associations, and in some instances by institutions of higher learning.

The Distance Learning Facility will provide health care professionals with the ability to continue their education at a comfortable pace and will minimal interruption to their busy work days. The facility will be operated by a special software engine that will provide the lesson topics, conduct the examinations, and respond with grading of testing activity.

The Distance Learning Facility (DLF) will also provide a calendar of events for training seminars, conferences, and related events that contribute to health care professional certification and continuing education requirements. Corporate clients may utilize the facilities for scheduling courses or seminars in conjunction with educational institutions who will provide the educational credits.

Computer Based Training facilities have been used very successfully by the computer industry for many years. A short time ago, CBT facilities have been implemented by universities and colleges for their educational programs providing students with the ability to complete educational credit requirements from a facility off-campus. In the late 1980's, higher education institutions began using a derivative of the CBT methodology to implement Distance Learning for students, many of whom never attend classes on campus.

With the advent of the Internet's World Wide Web, the concept of Distance Learning and Computer Based Training matured and is currently being implemented by many large schools for their student body. Primarily, distance learning is utilized by individuals who, are already in the work place, and cannot afford the time necessary to attend formal classroom facilities on campus.

The Biosciences Corporation web site utilizes the capabilities of a special Distance Learning Facility (DLF) software engine to create, maintain and manage distance learning facilities for our corporate and higher education clients. This engine provides the capability to create a full function distance learning facility for health care professionals including physicians, nursing staff, and others. The distance learning facility engine can create DLF courses that are high level general interest in scope, through detailed highly specialized courses that are useful to professionals in maintaining their skills and knowledge base.

The DLF engine will enable a corporate client to create a special program that is oriented toward their product line, with associated specialized knowledge content that would encourage health care professionals to participate and provide a forum for marketing their products. Corporate clients could also create a learning package in conjunction with an institution of higher education that would provide professionals with qualified instruction and information in their specialty fields.

The DLF facility could also be used by corporate entities to construct a combination of web based distance learning with related seminars in various locations to encourage professionals to sign up and attend.

When a corporate client wishes to make use of the DLF facility, he/she must access a special portal through the Corporate Client home page. Clicking on this portal icon will activate the DLF engine and the user will be presented with a legal agreement that must be completed for the creation to go forward.

The agreement will stipulate that a setup fee will be charged for the initial creation of the DLF entries. When the DLF is published, the service will receive a fee for each participant who accesses and utilizes the courseware.

Once the agreement has been completed, the user or initiator will be presented with a screen that will enable the courseware setup process. The initiator will indicate whether the courseware is to be constructed using the DLF engine or whether the courseware is already developed by the corporation and will be downloaded to the site. If the courseware is to be downloaded, the initiator must attest that the courseware engine is already web compliant. If the Corporate-supplied courseware is not web compliant, the initiator must agree to submit the courseware to the Biosciences Corporation engine for migration.

In the initial processes, the initiator will be required in step 1402 to specify the qualifier settings for the course to be published. This will include the type of course such as drug protocol testing, drug or procedure interactions, specific health care specialty information, or other type of knowledge base information.

The initiator will then be required to identify the target audience, physician in a particular specialty, nursing specialties such as pediatric, ICU, or Coronary Care, hospital or clinic administrators, and health care technicians such as x-ray, pulmonary, or laboratory techs.

If there is to be a seminar conducted in association with the courseware, the initiator will enter the date, time and location of the seminar. If there are to be multiple seminars in various location cities, the initiator will enter a link to the seminar calendar and ensure that the related information is entered into this facility as well.

The DLF Engine will present a form to describe the course synopsis. If the course is primarily dedicated to a specific product developed by the company, this must be clearly stated in the synopsis.

Existing courseware can be migrated in step 1404. Prior to initiating the DLF Engine migration activity, the initiator will be required to attest that the courseware to be migrated can be implemented legally without encountering any copyright infringement problems. This certification form must then be printed by the initiator and faxed or mailed to the Biosciences Corporation offices for filing. The migration will continue while this activity is being completed, but the courseware will not be published to the web site until the necessary legal document is received and recorded by Biosciences Corporation.

The DLF Engine will then access the downloaded file and extract the subject matter entries. The engine will then format the entries as if the initiator had entered them through the CREATE facility within the DLF Engine. When the migration process has been completed, the DLF Engine will store the courseware in a special table until cleared by Biosciences Corporation staff for publication. The initiator will then have the opportunity of reviewing the migrated course content and can make any updates, modifications, corrections, etc as appropriate.

The DLF Engine will then link the migrated courseware to the qualifier data records and prepare the courseware file for presentation on the PhysicianConnect web site home page. The course title and synopsis will be entered into the DLF area listing for review by the health care professional subscribers.

The corporate subscriber has the option of creating a courseware file using the Biosciences Corporation DLF Engine Course Creator in step 1406. This facility will function similar to the Interview Questionnaire Engine facilities in that it will enable the initiator to enter course information, questions, etc. as well as prompt the participant for responses or answers.

The DLF Course Creator Engine will prompt the initiator for the type of course, lecture or information only, information with question and answer, and information with solicitation for study participation. If the course includes an associated formal seminar the DLF Engine will prepare a sign up form for the participant to complete if she or he wishes to attend the seminar.

As with the Interview Questionnaire Engine, the Course Creator will provide the initiator with a review of the entries on demand. At each entry completion, the engine will offer the opportunity for a review of the entry or a review of the entries completed to that point.

Should the initiator wish to halt the process, the engine will save the entries with a book mark at the last completed entry point. When the initiator wishes to restart the process, the engine will pick up the processing at the previously book marked point.

When the initiator has completed all entries for the courseware, the Engine will log the completed information in a publish table and offer the initiator the opportunity for one final review prior to the publishing activity. If the initiator chooses to review the course, the engine will present the entries in their entirety and the initiator will have the opportunity of making any final edit changes.

Once the initiator has indicated that the course is complete, the DLF engine will transfer the files to the public web area in step 1408 and prepare the course for viewing by the intended recipients. Using the qualifier entries to ascertain the targeted participants, the DLF Engine will insert an entry into the EDUCATION area of the home page. Whenever a health care subscriber logs onto the web site, and their area of interest matches the course entry, the new course title will be displayed as available.

At the corporate initiator's discretion, the DLF engine will distribute notification of the course availability to selected participants in step 1410, regardless of whether they are subscribers to the Biosciences Corporation web site. This notification process will key off of a previously submitted selection list supplied by the corporate initiator. The list must include the participant's name and e-mail address to enable the DLF notification function. When the e-mails are generated to the list participants, the web site's URL will be embedded within the message text. The participant will only have to click on the URL and will be connected to the web site. They will be offered the opportunity of subscribing to the web services, but will not be required to do so.

The DLF Engine will have certain administrative functions in step 1412 that operate independently of the corporate client, but will provide feed back to the initiator organization regarding the course activity. These functions will include;

Course Critique: at the completion of the selected courseware, the participant will be asked to complete a short critique of the content. This critique form will be a standard form generated by the DLF Engine and will accumulate the responses into a report for the corporate client.

Participant Count: this function will maintain a tally of the total number of participants who access the course material. It will also show the number who completed the course, the number who halted the course and did not return, and the scoring for each participant.

Participant Scoring: for those DLF courses that have an exam format, the DLF engine will maintain a course scoring for those questions completed. This score will be provided to the participant at the end of the course material. A hard copy output will be available for the participant if desired.

Archival Function: the DLF engine will archive the course offering following a specified period of access. This access period will be determined by the corporate initiator during the initial setup activity. The archived course file will be maintained on the Biosciences Corporation archive server for a period of 6 months prior to deletion. Corporate clients may request a longer period of retention or may elect to have the course deleted at the end of the availability period. If the course is to be archived a small storage fee will be charged for each month of the retention period.

Accounting Function: the DLF Engine will maintain the necessary counts of usage, storage, length of course and other information to provide an set of accounting records that will be used by Biosciences Corporation in billing reconciliation.

A software architecture for implementing the preferred embodiment on the server 112 will now be described.

There are three major engines that drive the system: an access engine, an interview engine and a match engine. The access engine controls access to various applications in the system. The interview engine is an interactive facility for specifying information of interest, and the match engine is a searching and matching engine that matches requests to provisions.

The system includes a comprehensive database of users, expertise, requests, and provisions. This database maintains the information needed by the access engine to ensure proper user access, needed by the interview engine to ask the proper questions, and needed by the match engine to match requests to provisions.

Figure 15:
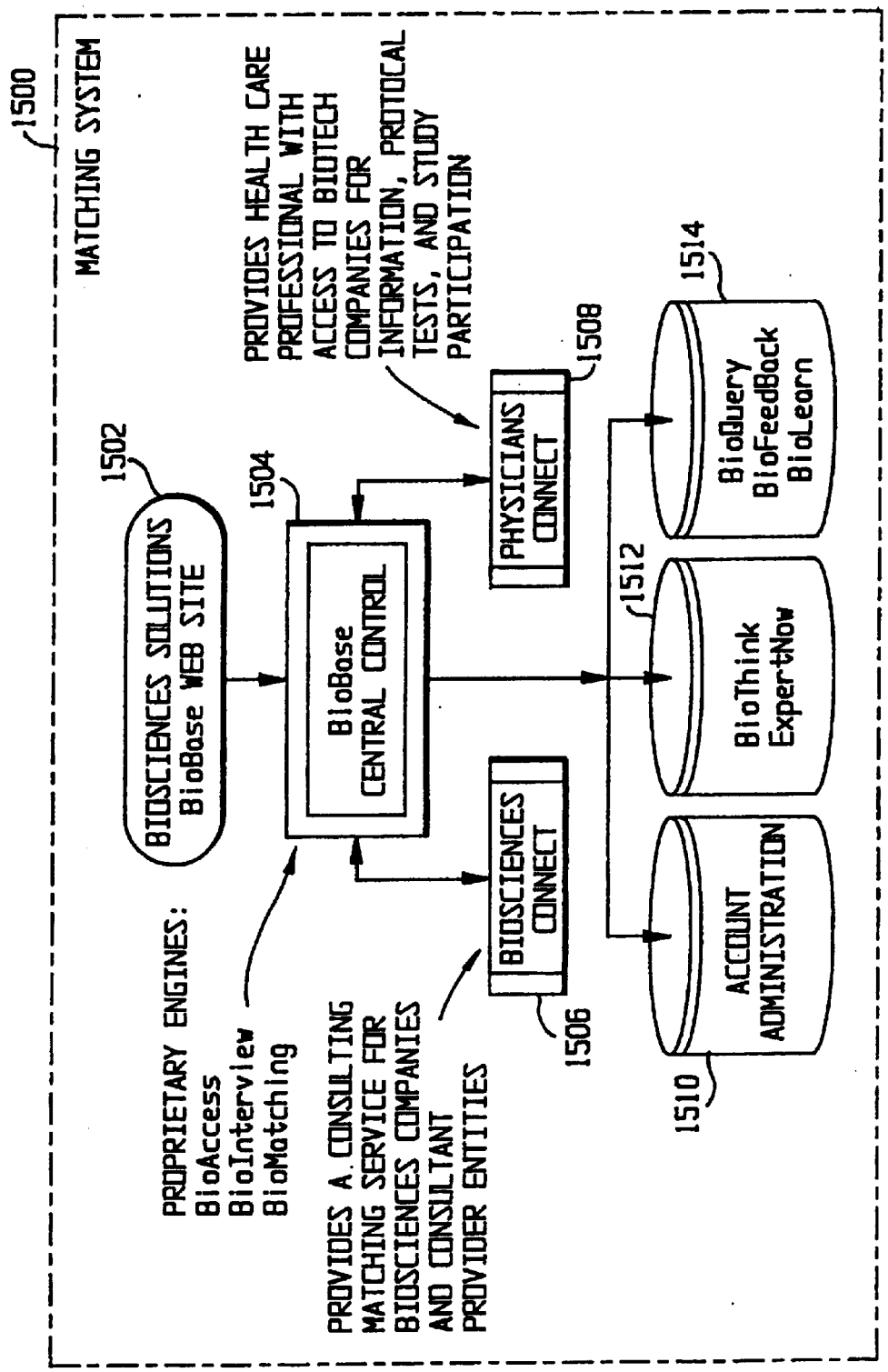
FIG. 15 shows a schematic diagram of the software components of the system of FIG. 1.

The architectural design of the system is presented in FIG. 15, which is implemented on the server 112 of FIG. 1. Access to the system 1500 is provided through a Web site 1502 and a central control module 1504. The central control module 1504 allows access to a consulting matching service 1506, which provides the above-described service of matching persons offering expert services with companies needing such services, and to an information access service 1508, which performs the above-described services of allowing persons to access companies for product information, protocol tests and study participation. Also provided are three databases: an account administration database 1510, which handles account status, payment, logon authorization and the like; a database 1512 used for the matching service 1506; and a database 1514 used for the information access service 1508.

When a user attempts to access the system, the access engine takes control. The user is presented with a logon screen to allow him to identify himself via a userID and password. If the user has not registered to use the system, he is given the option to register. If the user's registration (subscription) has expired, he is given the option to renew his registration. When the user is authenticated, the system creates a user session to allow the user to access the applications for which he is authorized. The access engine continues to monitor the user's activities to ensure that the user does not access any applications for which he is not authorized.

Figure 16:
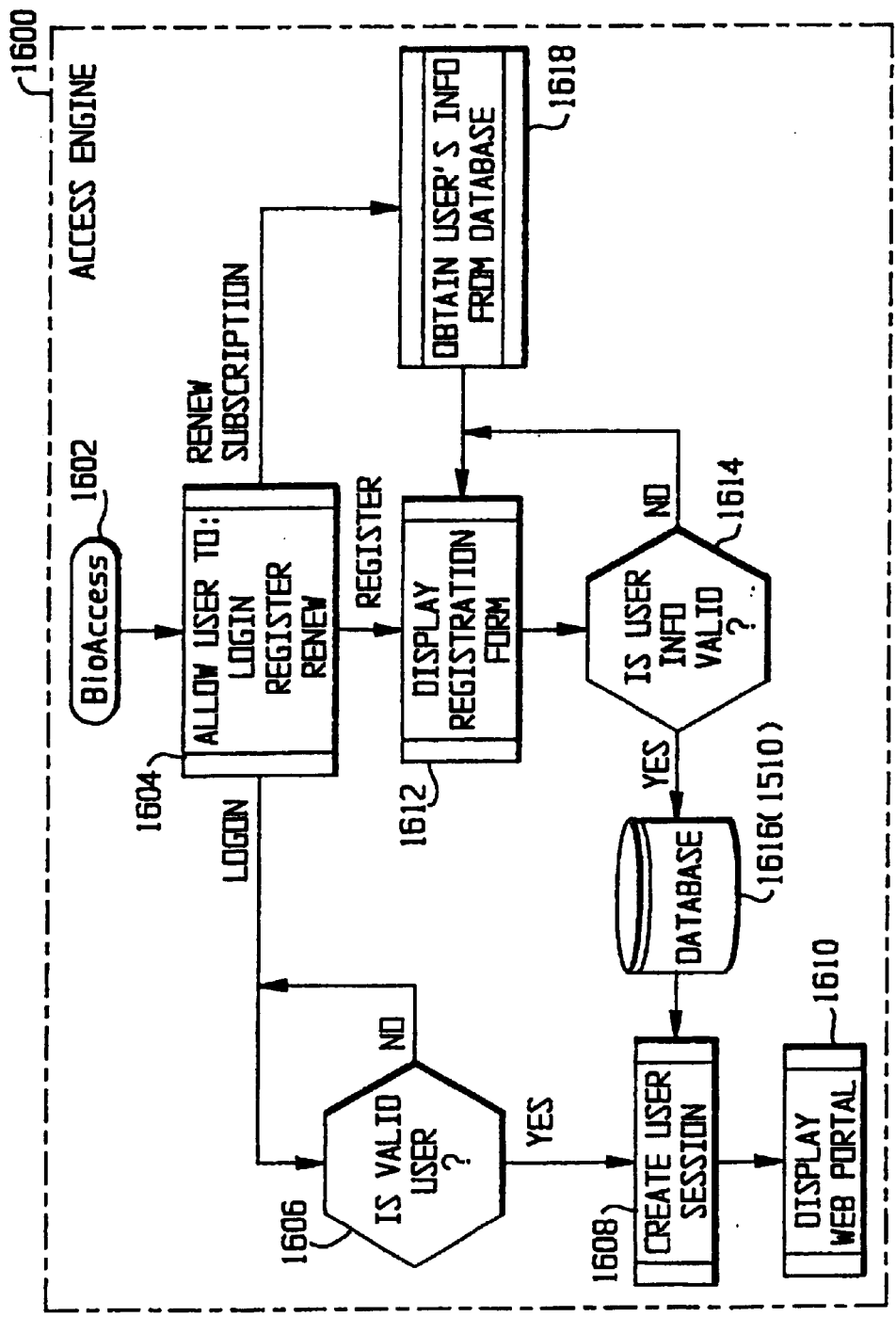
FIG. 16 shows an access engine which manages the logon procedure.

The design of the access engine 1600 is shown in FIG. 16. When a user attempts to access the service through the Access web page 1602, the access engine 1600 determines at 1604 whether the user is attempting to log on with an existing subscription, register to establish a new subscription or renew a subscription. If the user is attempting to log on with an existing subscription, the user's userID and password are validated in step 1606. If the userID and password are valid, a user session is created in step 1608, and the Web portal is displayed in step 1610. If the user is attempting to register, a registration form is displayed in step 1612. Once the user enters information, its validity is checked in step 1614. If the user information as entered is valid, the user is entered into the database 1510 in step 1616, and a user session is created in step 1608. If the user is attempting to renew a subscription, the user's information is obtained from the database 1510 in step 1618, and the registration form is displayed in step 1612.

On his first visit to the system, the user must register for the services which he wishes to use. This process begins with the display of a disclaimer page that the user must read and accept prior to continuing the registration process. Once the agreement is accepted, the new user is presented with a registration form.

The registration form allows the user to provide his contact information including full name, company name (if any), title (if any), contact address, contact telephone, and e-mail address. The user must also select the services he wishes to purchase.

Following the initial registration, the user is presented with a payment screen. This screen informs the user of the amount of the subscription fee and requests payment information, such as credit card number or purchase order number and billing address. If payment is via a credit card, a verification of the payment transaction is performed. If payment is via a purchase order, the purchase order is verified.

Once the payment transaction has been successfully completed, the user is presented with a userID and password selection screen. The user enters a userID, a password and a hint to assist the user in remembering his password. The system validates that the userID is not already being used. If the userID is being used, the user is asked to select a different userID. Otherwise, the access engine notifies the new user of a successful completion of the registration, emails the registration information to the user, and informs the user of password protection responsibilities. After the user accepts his password protection responsibilities, he is transferred to the appropriate portal web page for the application he wishes to use. This page is either a selection of which portion of the system he wishes to enter based on his subscriptions, or if only one services is subscribed to, is the start page for that service.

The user may renew his subscription at any time. Although this process is similar to registration, the user is allowed to continue the use of his current userID and password as long as there has not been more than a 30-day lapse in the subscription.

When renewing a subscription, the user goes through the same process as registration with the exception that the information previously provided is displayed for modification or verification.

Upon access to the system, the user is presented with a logon screen to allow him to identify himself via a userID and password. Once the user is authenticated, he is transferred to the appropriate portal web page. This page is either a selection of which portion of the system he wishes to enter based on his subscriptions, or if only one services is subscribed to, is the start page for that service.

If the user forgets his userID or password, he may contact the customer service representative for assistance. The representative may provide the user with the userID and hint. If the user is still unable to access the system, the representative may reset the user's password only after the user verifies the last four digits of his credit card or purchase order number. Various other ways of assisting a user who has forgotten his userID or password are known in the art and can be used as business considerations permit.

When a user enters an area of the system which requires user input, the interview engine takes control. The interview engine allows the user to specify what he requires or what he is providing via an interactive question and answer facility. This facility is made up of categories and subcategories which may be selected and then ranked according to a level of expertise and priority. For example, when identifying himself as a provider of expert services, the user selects the categories and subcategories for which he has expertise and indicates his level of expertise in each subcategory, as explained above. When identifying himself as a customer of expert services, the user selects the categories and subcategories for which he requires information and indicates the expertise level and priority (importance) of each subcategory, as also explained above. Level of expertise and priority are indicated as a number between 1 and 5, where 1 is highest and 5 is lowest.

The interview module includes categories which branch to subcategories based on specific areas of specialization within the biosciences field. This enables the user to refine their area of expertise or request criteria as well as provide a ranking of the level provided or requested. When used for entering requests for an expert, the interview module also allows the user to select a priority for the area of expertise.

As each section of the interview questionnaire is completed, the Requestor is presented with a display showing his entries. The interview module asks if the information is correct, or if the submitter wants to make any changes. If the Requestor indicates that changes are desired, the system returns to the data entry form of that section of the questionnaire for any edits or modifications. Following the completion of the questionnaire process, the Requestor has the option of requesting a printed copy of his entries.

Throughout the interview process, the subscriber may stop the activity and return later to complete the process.

When the interview process is halted, the Interview Engine inserts a book mark at the point where the process was interrupted. When the subscriber resumes the interview process, the Interview Engine pickups the questionnaire segment at the point of interruption.

Figure 17:
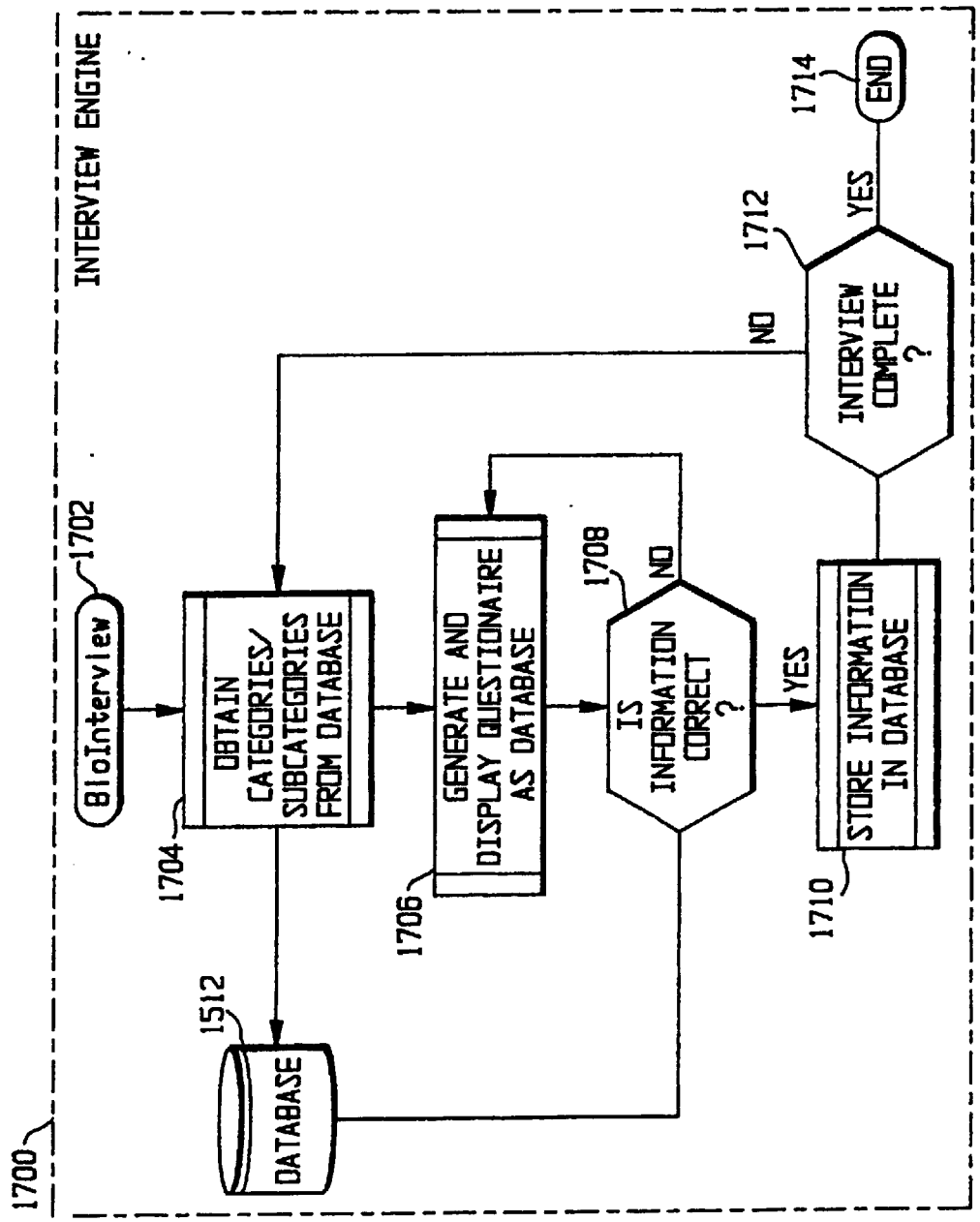
FIG. 17 shows an interview engine which manages the procedure for obtaining information on an expert's qualifications.

The design of the interview engine 1700 is depicted in FIG. 17. The person being interviewed is presented with an interview Web page in step 1702. The categories and subcategories are obtained in step 1704 from the database 1512, and a questionnaire web page is generated and displayed in step 1706. The information is validated in step 1708 and, if the validation is successful, stored in step 1710 in the database 1512. In step 1712, it is checked whether the interview is complete. If not, the process returns to step 1704. If so, the process ends in step 1714.

The match engine handles matching requests to provisions. For example, the match engine matches experts to service requesters. When using the learning feature, the match engine will search the database for all publications, seminars, courses, and advisors who match the requester's criteria. In both systems, the match engine searches the database for all provisions that match at least some of the requirements. It then determines how close a match was found via a mathematical formula that takes into account the level of expertise requested, the priority (importance) of the expertise requested, and the level of expertise provided. The mathematical formula is for determining rank is as follows:

$$\frac{20 * \sum (5 - \text{MAX}(0, (ProviderLevel - RequesterLevel))) * (6 - \text{Priority})}{\sum (6 - \text{Priority})}$$

The rank is thus a weighted average of the difference between provider and requester levels, with the priority assigned by the requester to each entry as the weighting factor.

The match engine is launched immediately by the user from the portal or may be initiated as a scheduled activity. The match engine may be launched by both Requestors and Providers to search for possible matching records. When executed immediately, the user is provided with a summary list of matches and a ranking of those matches via a web page. When scheduled, the match engine runs on a periodic basis and sends an email to the requester informing him of any matches found. The requester may then enter the portal to view the matches. Upon entry into the portal, the user is informed that matches were found and is allowed to view the matches via a web page.

The match engine displays a summary list of matches and a ranking of those matches via a web page. The user has the option of viewing each record in detail and obtaining contact information for a fee. When the user selects to view the detailed record, he must accept payment of a fee. The user's payment information is displayed and the user has the option of changing the method of payment or accepting the current payment method. Once payment has been processed, the detailed record is displayed in a web page and emailed to the user.

Figure 18:
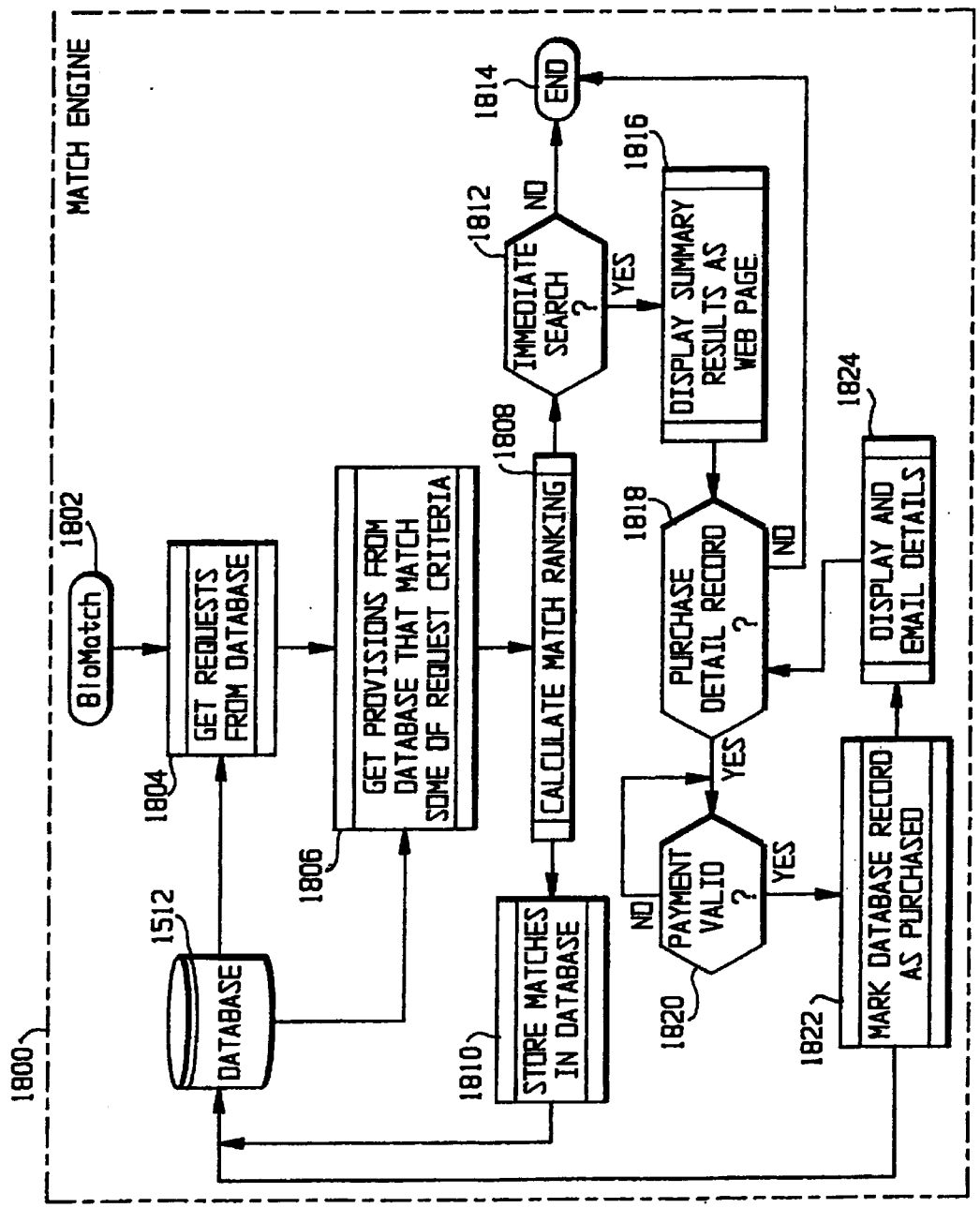
FIG. 18 shows a match engine for matching providers of expert services with requesters of expert services.

The design of the match engine 1800 is as displayed in FIG. 18. The match process begins in step 1802, when either a requester makes a request or the match engine is controlled to run periodically. Requests are retrieved in step 1804 from the database 1512, and database entries that match some of the request criteria are retrieved in step 1806. The match rankings are calculated according to the above formula in step 1808 and are stored in step 1810 in the database 1512.

In step 1812, it is determined whether the match calculation is periodic or is done in response to an immediate (user-requested) search. If the match calculation is periodic, the process ends in step 1814. If the calculation is done in response to an immediate search, the summary results are displayed in step 1816. It is then determined in step 1818 whether the requester has requested to purchase a detailed record; if so, it is determined in step 1820 whether the proffered payment method is valid. If the payment method is valid, the database record is marked as purchased in step 1822, and the details are displayed and e-mailed in step 1824.

The database is designed to allow expansion of the expertise and other criteria set during the Interview process. New criteria may be added without redesigning the database or applications. This is possible via the Categories and Subcategories tables.

Figure 19:
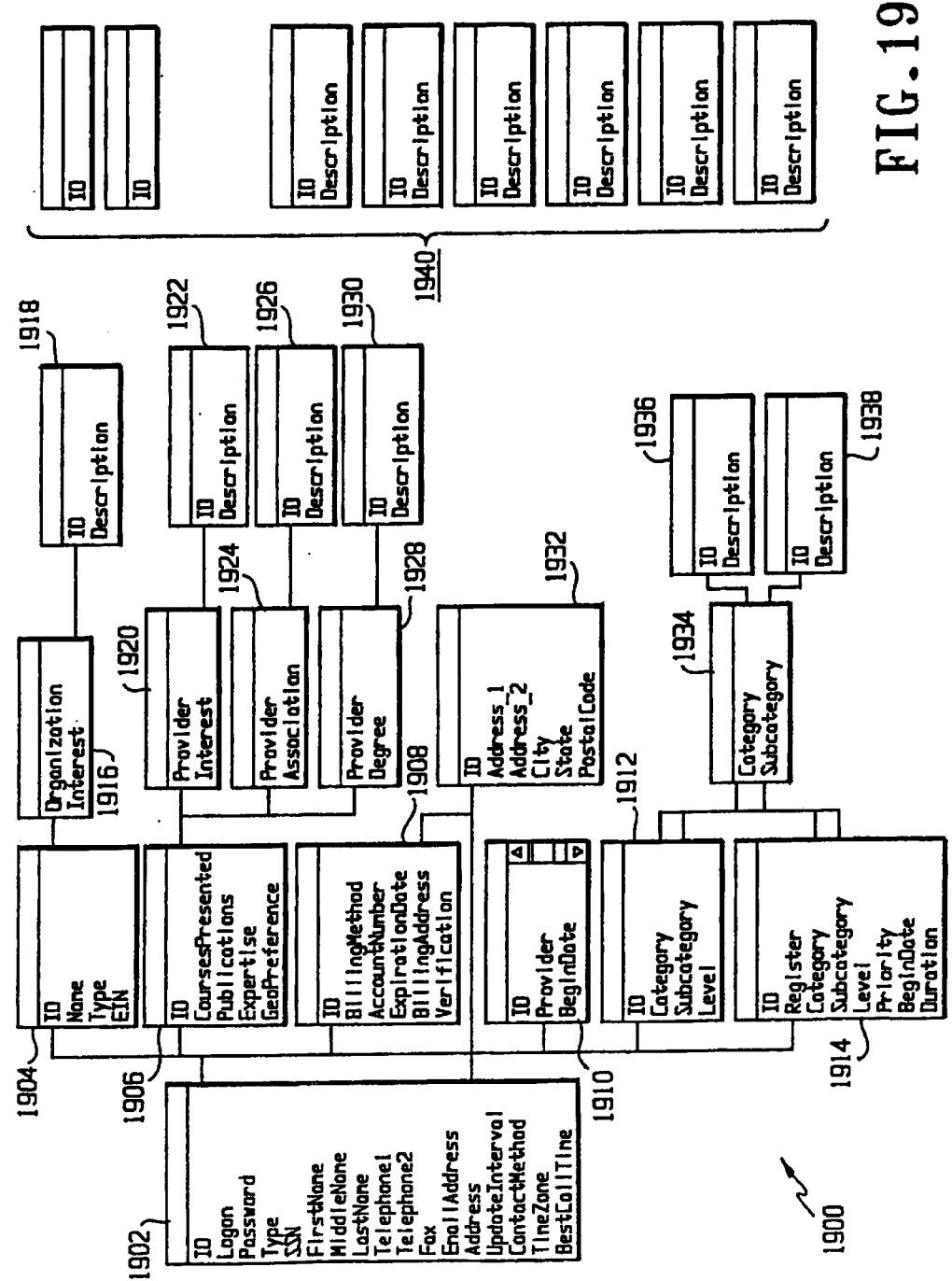
FIG. 19 shows an organization of a relational database for storing information on subscribers to the service.

The database tables and their interrelationship are shown in FIG. 19. The relational database 1900 is based on a database table 1902 identifying a registered user and having the following fields: ID, logon, password, type of user, Social Security number, first name, middle name, last name, two telephone numbers, a facsimile number, an e-mail address, an address, an update interval, a contact method, a time zone in which the user is located, and a best time to call. The table 1902 is linked via the ID field to six other tables. The table 1904, used if the user is an organization, includes fields for the ID, the name, the type of organization and the federal employer I.D. number. The table 1906, used if the user is an individual, has fields for the ID, the courses presented by that person, that person's publications, that person's expertise and that person's geographic preference for work. The table 1908 is used for accounting and has fields for the ID, the billing method, the account number, the expiration date, the billing address and verification. The table 1910 is used for providers of knowledge services and has fields for the ID, the name of the provider and the beginning and ending dates. The table 1912 is also used for providers of knowledge services and has fields for the ID, a category and a subcategory of the person's knowledge specialties, and the level of expertise. A single person's ID can be linked to multiple tables 1912 to cover all of that person's specialties. A table 1914 is used for requesters of knowledge services and includes fields for the ID, the requester name, the category and subcategory, the level of knowledge required in that specialty, the priority that the requester has assigned to that category and subcategory, and the required beginning date and duration. A single requester's ID can be linked to multiple tables 1914.

The tables 1904–1914 are further linked to additional tables as follows. The table 1904 for the organization is linked to a table 1916 giving an organization interest, which is linked to an ID/description table 1918. The table 1906 is linked to a provider interest table 1920, a provider association 1924 and a provider degree table 1928, each of which is linked to an ID/description table 1922, 1926 or 1928. The tables 1902 and 1908 are linked to a table 1932 having fields for the ID, two lines of the address, and the city, state and ZIP code. The tables 1912 and 1914 are both linked by the category and subcategory fields to a category and subcategory table 1934, which is linked to a category ID/description table 1936 and a subcategory ID/description table 1938.

The ID/description tables provide detailed descriptions of the items to which they are linked. For instance, the provider degree ID/description table 1930 includes an ID field identifying a provider's degree to link that table to a provider degree table f1928 and a free-dorm description of that degree. Similarly, the subcategory ID/description table includes an ID field identifying the subcategory and a free-form description of what that subcategory entails. Additional ID/description tables 1940 are provided for expansion purposes.

The database should preferably meet the following criteria: It should be implemented in an ODBC-compliant, relational database management system. The implementation method should allow for the creation of user sessions and should allow for the dynamic creation of web pages. Multiple sessions of the same application should share a database connection. User passwords should be maintained in encrypted form in the database. User credit card numbers should be maintained in encrypted form in a separate database. The database should be password protected with strict access controls, and reverse encryption should preferably be possible. The last four digits of the user's credit card will be maintained in unencrypted form in the database to allow the user to authenticate himself to technical support staff, as described above.

While a preferred embodiment has been set forth in detail above, those skilled in the art will readily appreciate that many other embodiments can be realized within the scope of the invention. For example, the invention is not limited to experts in the biological sciences, but can be extended to other areas of expertise, such as computer consulting. For that matter, the invention need not be limited to expert services at all, but can be used for any type of matching of a first party to a second party in which it is desired to develop a longitudinal picture of availability. Moreover, while the invention has been disclosed as implemented on the World Wide Web, any other suitable communication technology can be used instead. Therefore, the present invention should be construed as limited only by the appended claims.

What is claimed is:

1. A memory for storing data in a computer, the memory comprising:
   a computer-readable storage medium;
   (1) at least one user data structure stored in said medium, the user data structure comprising data concerning one or more users, wherein, for each user, the user data structure includes one or more fields providing contact information for the user, wherein the user is an expert or a customer;
   (2) an expert data structure stored in said medium, the expert data structure comprising data concerning one or more experts, wherein, for each expert, the expert data structure includes
      (a) one or more fields defining at least one time period of availability of the expert for performing a project, and
      (b) one or more fields defining at least one category of expertise or experience of the expert and a level of expertise or experience of the expert with respect to each said category;
   (3) a project data structure stored in said medium, the project data structure omprising data concerning one or more projects, wherein, for each project, there project data structure includes
      (a) one or more fields identifying a customer within said user data structure,
      (b) one or more fields defining at least one desired time period of availability of an expert for performing the project,
      (c) one or more fields defining a desired level of expertise or experience of the expert for performing the project in each of one or more categories of expertise or experience, and
      (d) one or more fields defining a level of priority to the customer within said user data structure for the project, of expertise equaling or exceeding each of the desired levels of (c) above, said priority being specifiable independently of a desired level of expertise; and
   (4) a match data structure resulting from comparison of said expert data structure with said project data structure, said match data structure assigning to each expert a match score taking into account a level of expertise or experience of an expert in each of one or more of categories of expertise or experience, a level of expertise desired by a customer in each of one or more of said categories, and a priority assigned by the customer to expertise in each of said categories, wherein matches in said match data structure are ranked, wherein the ranking is a weighted average, over categories specified as desired by the customer, of a difference between expert's level of expertise and customer's desired level of expertise, with customer's priority for each category being a weighting factor.

2. The memory of claim 1, wherein an expert is an expert in biological sciences and the categories of expertise or experience relate to the biological sciences.

3. The memory of claim 2, wherein for each expert, a level of expertise or experience is defined on a hierarchical basis consisting of at least two tiers, and for each project, a desired level of expertise or experience and a priority of the desired level is defined on a hierarchical basis consisting at least two tiers.

4. The memory of claim 1, further comprising a data structure indicating availability of contact information on one user to another user.

5. The memory of claim 1, wherein for each expert, a level of expertise or experience is defined on a hierarchical basis consisting of at least two tiers, and for each project, a desired level of expertise or experience and a priority of the desired level is defined on a hierarchical basis consisting at least two tiers.

6. The memory of claim 1, further comprising:
   (5) an access control data structure stored in said medium, the access control data structure comprising one or more fields specifying each user's access to confidential information fields concerning another user, and the access control data structure permitting an access of an expert to confidential information of a customer to be controlled separately from an access of a customer to confidential information of an expert.

7. The memory of claim 1, wherein for each expert, a level of expertise or experience is defined on a hierarchical basis comprising at least two tiers, and for each project, a desired level of expertise or experience and a priority of the desired level is defined on a hierarchical basis comprising at least two tiers.

* * * * *